(12) United States Patent
Akagane

(10) Patent No.: US 9,474,568 B2
(45) Date of Patent: Oct. 25, 2016

(54) ENERGY BIPOLAR TREATMENT DEVICE

(71) Applicant: OLYMPUS CORPORATION, Hachioji-shi, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/630,952

(22) Filed: Sep. 28, 2012

(65) Prior Publication Data
US 2013/0116686 A1 May 9, 2013

Related U.S. Application Data

(63) Continuation of application No. PCT/JP2012/055576, filed on Mar. 5, 2012.

(60) Provisional application No. 61/450,760, filed on Mar. 9, 2011.

(51) Int. Cl.
A61B 18/14 (2006.01)
A61B 17/32 (2006.01)
A61B 18/00 (2006.01)

(52) U.S. Cl.
CPC ... *A61B 18/1442* (2013.01); *A61B 17/320068* (2013.01); *A61B 18/1445* (2013.01);
(Continued)

(58) Field of Classification Search
CPC .............. A61B 18/14; A61B 18/1442; A61B 18/1445; A61B 18/1447; A61B 18/18; A61B 18/1815; A61B 2018/00291; A61B 2018/00011; A61B 2018/0225; A61B 2018/1452; A61B 17/320092; A61B 17/29; A61B 17/320016; A61B 17/00234; A61B 17/320068; A61B 17/0218; A61B 2017/00473; A61B 2017/320044; A61B 2017/2215; A61B 2017/320028; A61B 2218/002; A61B 2218/007; A61B 10/06
USPC ................................ 606/41, 42, 50–52, 169
See application file for complete search history.

(56) References Cited

U.S. PATENT DOCUMENTS 4,013,079 A * 3/1977 Lindemann et al. ......... 606/191
4,535,759 A * 8/1985 Polk et al. ........................ 601/2
(Continued)

FOREIGN PATENT DOCUMENTS

DE 10 2009 013 468 A1 9/2010
EP 2 106 762 A1 10/2009
(Continued)

OTHER PUBLICATIONS

Apr. 3, 2012 Search Report issued in International Patent Application No. PCT/JP2012/055576.
(Continued)

*Primary Examiner* — Michael Peffley
*Assistant Examiner* — Khadijeh Vahdat
(74) *Attorney, Agent, or Firm* — Oliff PLC

(57) ABSTRACT

An energy treatment device includes a probe in which a suction path is defined inside along a longitudinal axis to a distal surface portion. The probe includes a first protrusion protruding an outer peripheral distal end of an outer peripheral portion toward a first perpendicular direction perpendicular to the longitudinal axis and perpendicular to open/close directions of the jaw. The distal surface portion includes an inclined plane in which it goes toward a distal direction side as it goes from the first perpendicular direction toward a second perpendicular direction that is opposite to the first perpendicular direction, the inclined plane extending from a first end position, located to the first perpendicular direction side of a first root position of a first protrusion, to a second end position, located to the second perpendicular direction side of the suction path.

3 Claims, 14 Drawing Sheets

(52) U.S. Cl.
CPC ........... *A61B2018/00607* (2013.01); *A61B 2018/00994* (2013.01); *A61B 2217/007* (2013.01); *A61B 2218/007* (2013.01)

(56) References Cited

U.S. PATENT DOCUMENTS

| | | | |
|---|---|---|---|
| 5,217,460 | A | 6/1993 | Knoepfler |
| 5,300,087 | A | 4/1994 | Knoepfler |
| 5,944,717 | A | 8/1999 | Lee et al. |
| 6,139,561 | A * | 10/2000 | Shibata et al. ............ 606/169 |
| 6,371,973 | B1 * | 4/2002 | Tepper ............ 606/205 |
| 6,669,690 | B1 | 12/2003 | Okada et al. |
| 6,840,938 | B1 | 1/2005 | Morley et al. |
| 2003/0120268 | A1 | 6/2003 | Bertolero et al. |
| 2005/0004589 | A1 | 1/2005 | Okada et al. |
| 2005/0124987 | A1 | 6/2005 | Goble |
| 2008/0114355 | A1 | 5/2008 | Whayne et al. |
| 2009/0036914 | A1 | 2/2009 | Houser |
| 2009/0270854 | A1 | 10/2009 | Yachi et al. |
| 2010/0324458 | A1 | 12/2010 | Okada et al. |
| 2011/0004127 | A1 | 1/2011 | Okada et al. |
| 2011/0015631 | A1 * | 1/2011 | Wiener et al. ............ 606/42 |

FOREIGN PATENT DOCUMENTS

| | | |
|---|---|---|
| JP | A-2000-23994 | 1/2000 |
| JP | A-2002-78714 | 3/2002 |
| JP | A-2007-330723 | 12/2007 |
| JP | A-2010-535087 | 11/2010 |

OTHER PUBLICATIONS

Aug. 30, 2013 Search Report Issued in European Patent Application No. 12755074.7-1652.
Sep. 19, 2013 English Translation of the International Preliminary Report on Patentability issued in International Patent Application No. PCT/JP2012/055576.

* cited by examiner

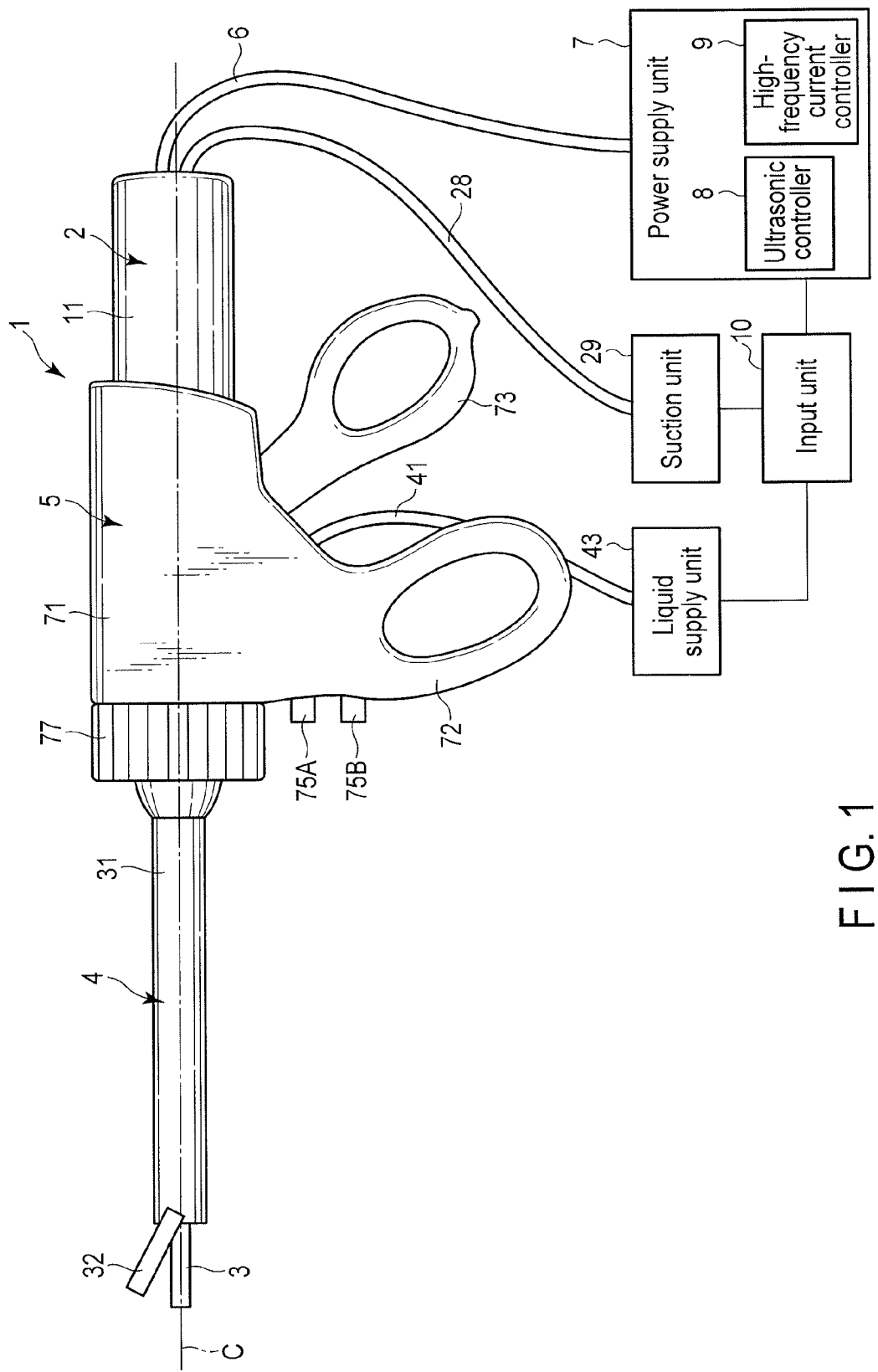
F I G. 1

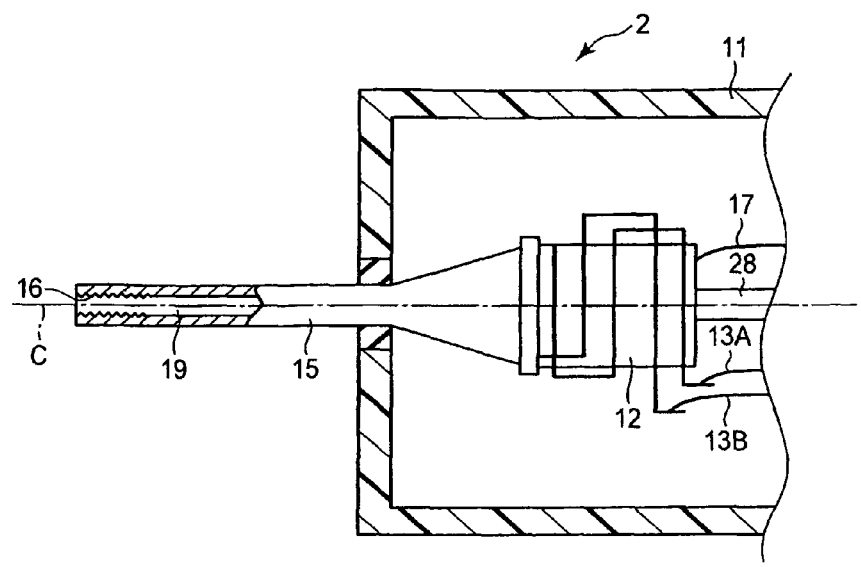
F I G. 2
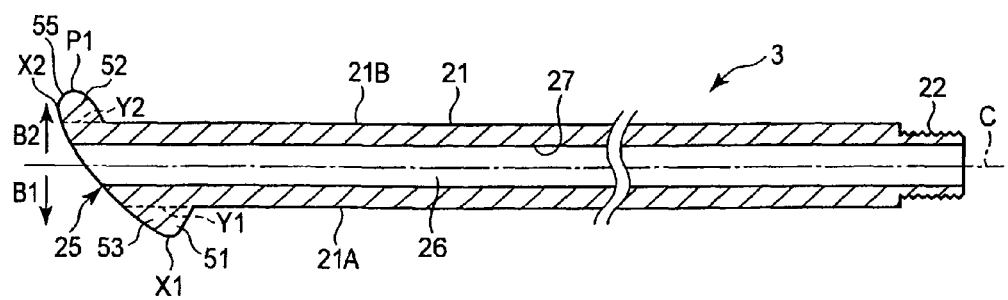
F I G. 3

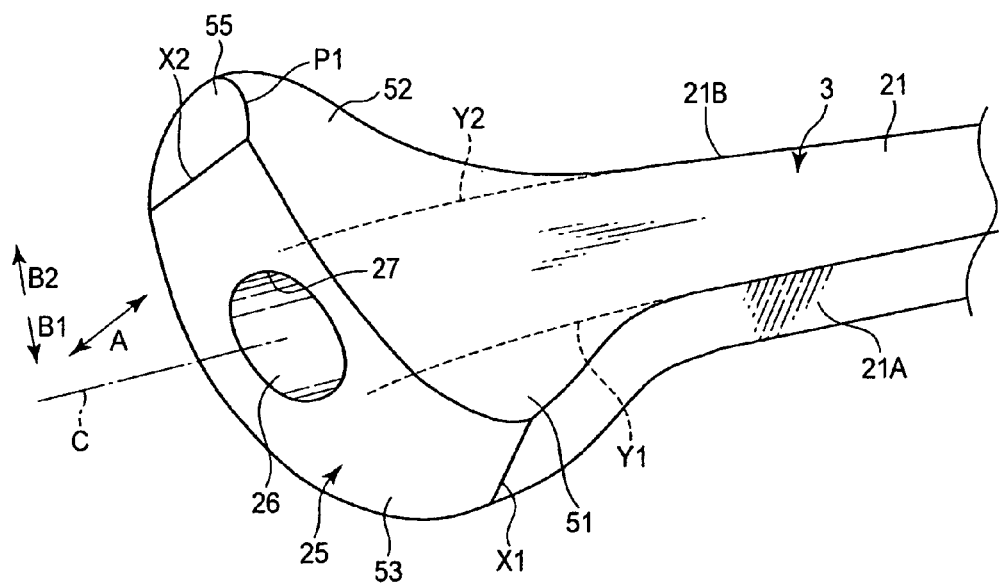
F I G. 4
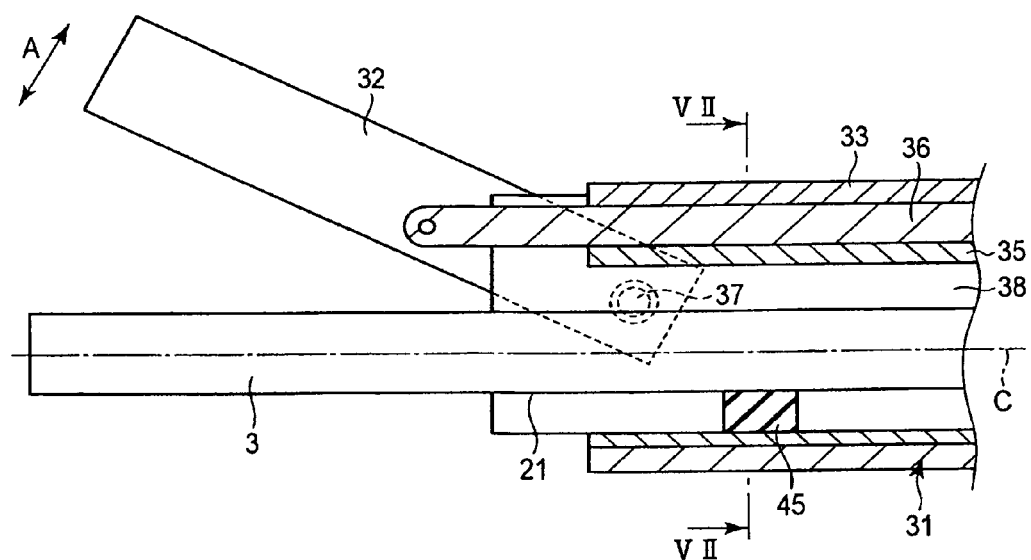
F I G. 5

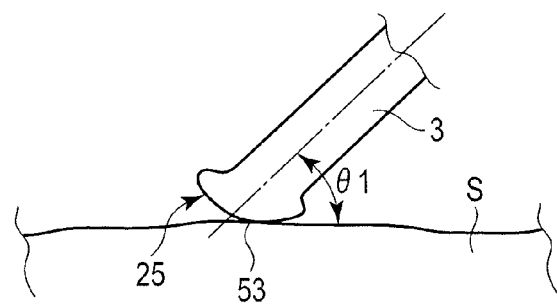
F I G. 13A
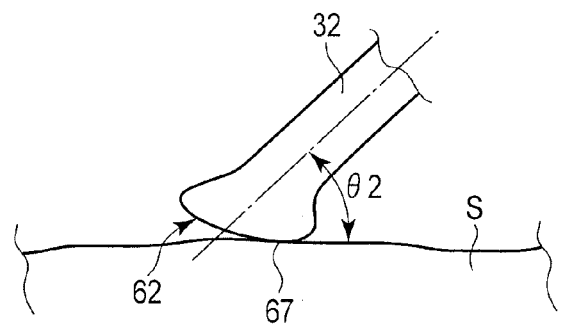
F I G. 13B
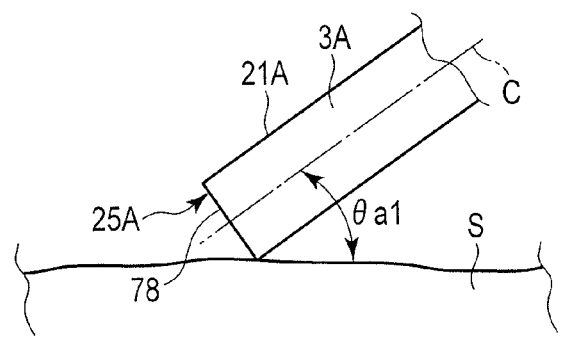
F I G. 14A

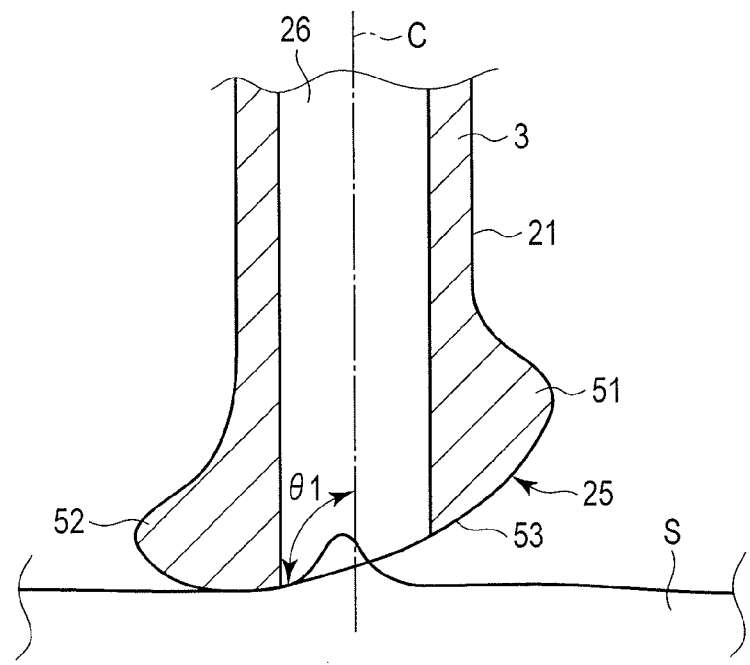
F I G. 20
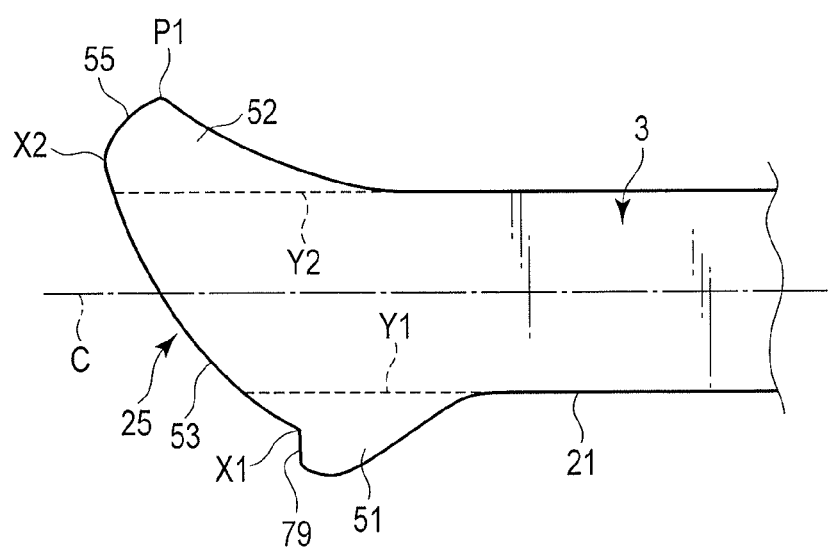
F I G. 21

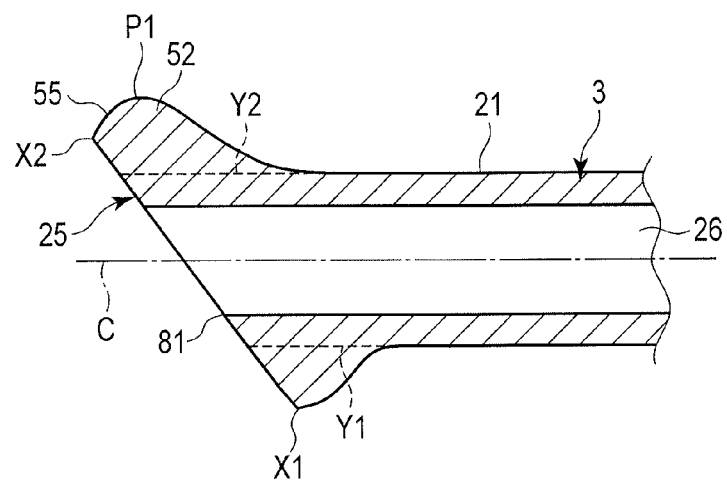
F I G. 24A
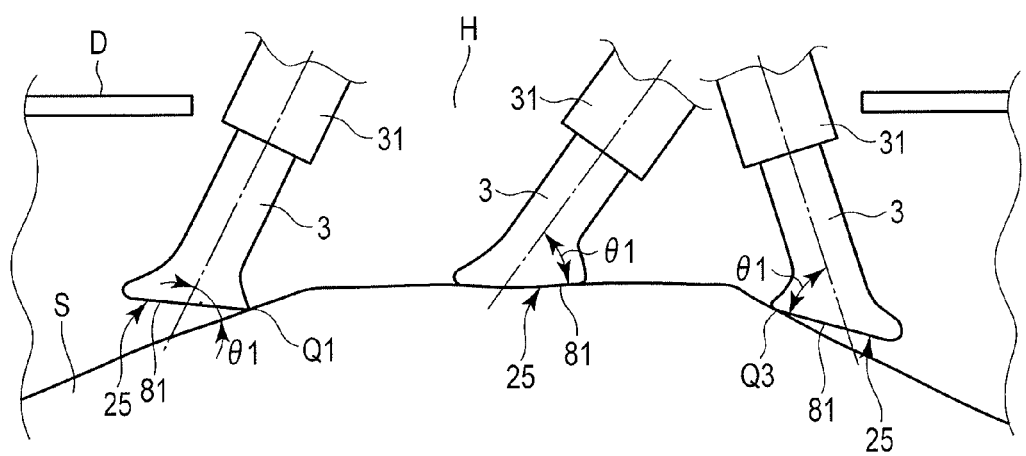
F I G. 24B

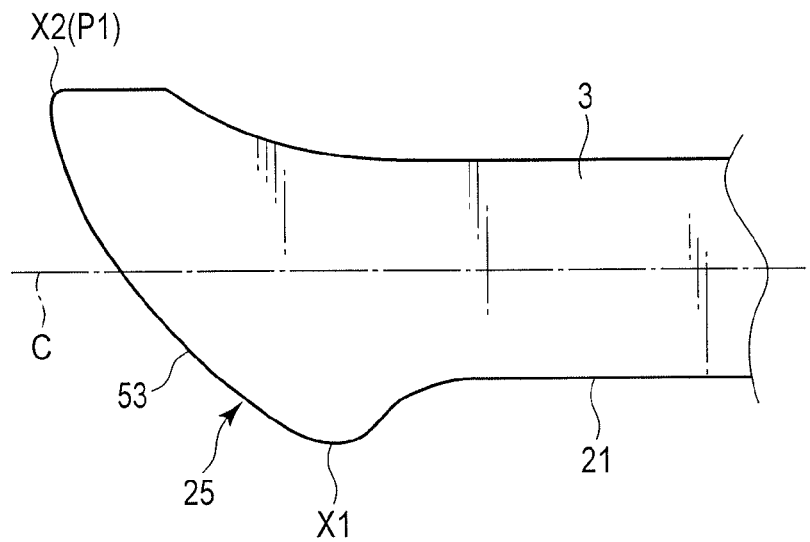
F I G. 25
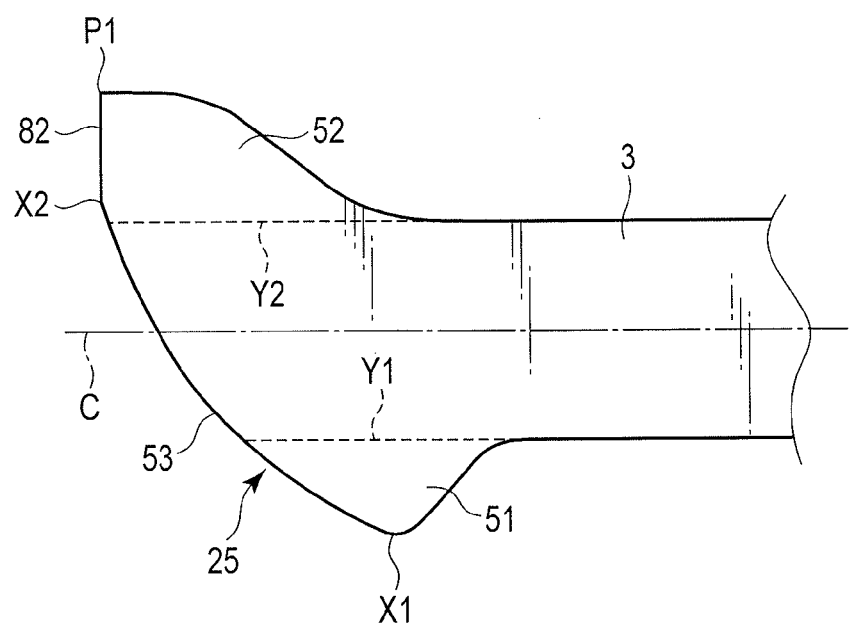
F I G. 26

ENERGY BIPOLAR TREATMENT DEVICE

CROSS-REFERENCE TO RELATED APPLICATIONS

This is a Continuation Application of PCT Application No. PCT/JP2012/055576, filed Mar. 5, 2012 and based upon and claiming the benefit of priority from prior U.S. Provisional Application No. 61/450,760, filed Mar. 9, 2011, the entire contents of which are incorporated herein by reference.

BACKGROUND OF THE INVENTION

1. Field of the Invention

The present invention relates to a bipolar treatment device which configured to use a probe and a jaw configured to open/close with respect to a distal portion of the probe as electrodes to perform a treatment by a high-frequency current.

2. Description of the Related Art

A medical treatment device disclosed in US2009/0270854 includes a columnar (non-hollow) probe extending along a longitudinal axis, and a jaw configured to open/close with respect to a distal portion of the probe. This medical treatment device is used as a bipolar treatment device which is configured to use the probe and the jaw as electrodes to perform a bipolar treatment by a high-frequency current. The distal portion of the probe is curved from a first perpendicular direction, which is perpendicular to the longitudinal axis and perpendicular to open/close directions of the jaw, toward a second perpendicular direction, which is opposite to the first perpendicular direction. As the distal portion of the probe is curved, an inclined plane inclined with respect to the longitudinal axis of the probe is formed in an outer peripheral surface of a curved part. The jaw is curved from the first perpendicular direction toward the second perpendicular direction in accordance with the curved shape of the probe. As the jaw is curved, a jaw-side inclined plane is formed in an outer peripheral surface of a curved part of the jaw.

In an example of the bipolar treatment by the high-frequency current, a probe and a jaw open with respect to the probe are used as electrodes to pass a high-frequency current through living tissue between the probe and the jaw via a supplied liquid such as a physiological saline solution, and the living tissue is coagulated by the high-frequency current. In this treatment, an inclined plane provided in the outer peripheral surface of the distal portion of the probe and a jaw-side inclined plane of the jaw are brought into contact with the living tissue while the jaw is open with respect to the probe. A liquid (physiological saline solution) is then supplied to the living tissue between the probe and the jaw, and the probe and the jaw are used as electrodes to pass a high-frequency current through the living tissue between the probe and the jaw via the supplied liquid. The liquid (physiological saline solution) is heated by the high-frequency current, and boils. The living tissue is reformed by using the boiling liquid, and coagulated. The living tissue can be efficiently and rapidly coagulated over a wide range by using the liquid (physiological saline solution) brought to boil by the principle described above. The intervention of the liquid (physiological saline solution) enables the living tissue to be coagulated so that the living tissue may not be excessively carbonized by the heat of the high-frequency current and so that the coagulated living tissue may not firmly adhere to the probe or the jaw.

BRIEF SUMMARY OF THE INVENTION

According to one aspect of the present invention, an energy treatment device includes that a probe, the probe including an outer peripheral portion extending along a longitudinal axis, a distal surface portion in which an outer peripheral distal end of the outer peripheral portion is an outer edge, and a path defining surface which defines a suction path inside the probe along the longitudinal axis from a proximal end of the probe to the distal surface portion; and a jaw configured to open/close with respect to a distal portion of the probe in directions perpendicular to the longitudinal axis, wherein the probe includes a first protrusion which protrudes the outer peripheral distal end of the outer peripheral portion toward a first perpendicular direction, that is perpendicular to the longitudinal axis and perpendicular to open/close directions of the jaw, the distal surface portion of the probe includes an inclined plane in which it goes toward a distal direction side as it goes from the first perpendicular direction toward a second perpendicular direction, that is opposite to the first perpendicular direction, the inclined plane extending from a first end position to a second end position, the first end position being located to the first perpendicular direction side of a first root position which is a root position of the first protrusion, and the second end position being located to the second perpendicular direction side of the suction path, and the first root position of the first protrusion is located to the first perpendicular direction side of an opening of the suction path in the distal surface portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing a bipolar treatment device according to a first embodiment of the present invention;

FIG. 2 is a schematic sectional view showing the configuration of a vibrator unit according to the first embodiment;

FIG. 3 is a schematic sectional view showing the configuration of a probe according to the first embodiment;

FIG. 4 is a schematic perspective view showing the configuration of a distal portion of the probe according to the first embodiment;

FIG. 5 is a schematic sectional view showing a state in which the probe is inserted through a sheath according to the first embodiment;

FIG. 13A is a schematic diagram showing the contact between the probe and living tissue in the bipolar treatment performed while the jaw is open with respect to the probe according to the first embodiment;

FIG. 13B is a schematic diagram showing the contact between the jaw and the living tissue in the bipolar treatment performed while the jaw is open with respect to the probe according to the first embodiment;

FIG. 14A is a schematic diagram showing the contact between a probe and living tissue according to a first comparative example of the first embodiment;

FIG. 20 is a schematic diagram showing a state in which ultrasonic suction is performed by the probe according to the first embodiment;

FIG. 21 is a schematic diagram showing a distal portion of a probe according to a first modification of the first embodiment when viewed from one of open/close directions of the jaw;

FIG. 24A is a schematic sectional view showing the configuration of a distal portion of a probe according a fourth modification of the first embodiment;

FIG. 24B is a schematic diagram showing the contact between the probe and living tissue at various positions of the living tissue when a bipolar treatment is performed while a jaw is open with respect to the probe according to the fourth modification of the first embodiment;

FIG. 25 is a schematic diagram showing a distal portion of a probe according to a second embodiment of the present invention when viewed from one of open/close directions of a jaw; and FIG. 26 is a schematic diagram showing a distal portion of a probe according to a third embodiment of the present invention when viewed from one of open/close directions of a jaw.

DETAILED DESCRIPTION OF THE INVENTION

First Embodiment

Figure 6:
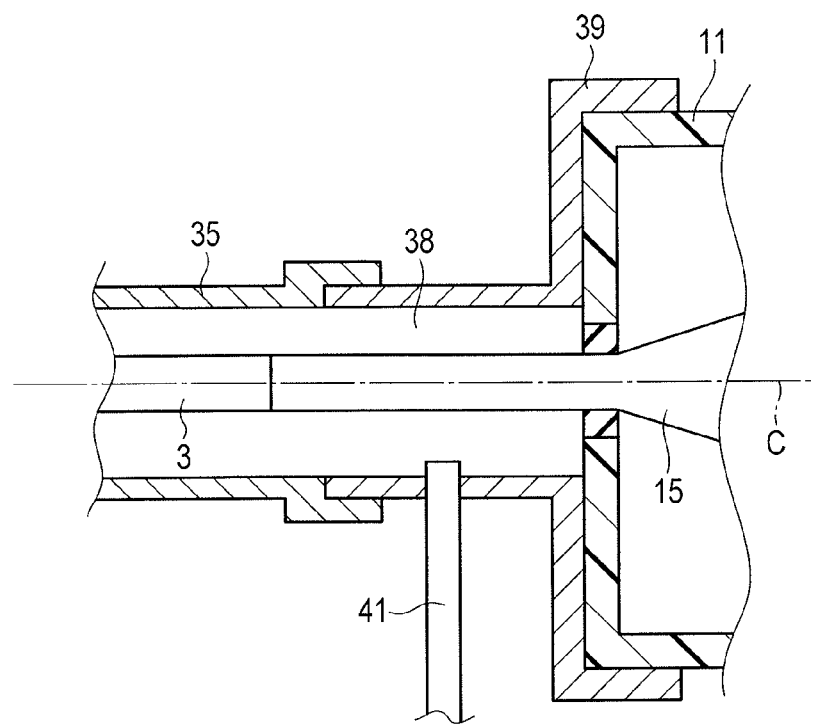
FIG. 6 is a schematic sectional view showing the configuration of a coupling portion between the sheath and a vibrator case according to the first embodiment.

A first embodiment of the present invention is described with reference to FIG. 1 to FIG. 20. FIG. 1 is a diagram showing a bipolar treatment device 1 according to the present embodiment. The bipolar treatment device 1 is configured to use a probe 3 (described later) and a jaw 32 (described later) as electrodes to perform a bipolar treatment by a high-frequency current. The bipolar treatment device 1 is also used as an ultrasonic suction device which is configured to selectively shatter and resect living tissue by cavitation caused by ultrasonic vibrations, and which is configured to suction the resected living tissue. That is, the bipolar treatment device 1 is an energy treatment device. As shown in FIG. 1, the bipolar treatment device 1 includes a vibrator unit 2, the probe (ultrasonic probe) 3, a sheath unit 4, and a handle unit 5.

The vibrator unit 2 includes a vibrator case 11. One end of a cable 6 is connected to a proximal end of the vibrator case 11. The other end of the cable 6 is connected to a power supply unit 7. The power supply unit 7 includes an ultrasonic controller 8, and a high-frequency current controller 9. An input unit 10 such as a foot switch is connected to the power supply unit 7.

FIG. 2 is a diagram showing the configuration of the vibrator unit 2. As shown in FIG. 2, an ultrasonic vibrator 12, which includes a piezoelectric element configured to convert a current to ultrasonic vibrations, is provided inside the vibrator case 11. One end of each of electric signal lines 13A and 13B is connected to the ultrasonic vibrator 12. The other end of each of the electric signal lines 13A and 13B is connected to the ultrasonic controller 8 of the power supply unit 7 through an inside of the cable 6. Ultrasonic vibrations are generated in the ultrasonic vibrator 12 by supplying a current to the ultrasonic vibrator 12 from the ultrasonic controller 8 via the electric signal lines 13A and 13B. A horn 15, which is configured to increase the amplitude of the ultrasonic vibrations, is coupled to a distal direction side of the ultrasonic vibrator 12.

The horn 15 is attached to the vibrator case 11, and electrically insulated from the vibrator case 11. In the ultrasonic vibrator 12 and the horn 15, a space portion 19, in which a longitudinal axis C is a centre, is formed. An internal thread 16 is formed in a distal portion of an inner peripheral surface of the horn 15. In addition to the electric signal lines 13A and 13B, an electric signal line 17, extending from the high-frequency current controller 9 of the power supply unit 7 through the inside of the cable 6, is connected to the ultrasonic vibrator 12.

FIG. 3 is a diagram showing the configuration of the probe 3. As shown in FIG. 3, the probe 3 includes an outer peripheral portion 21 extending along the longitudinal axis C. The outer peripheral portion 21 includes a first base outer surface 21A and a second base outer surface 21B. An external thread 22 to be screwed to the internal thread 16 of the horn 15 is provided in a proximal portion of the outer peripheral portion 21. When the external thread 22 is screwed to the internal thread 16, the probe 3 is attached to the distal direction side of the horn 15. When the probe 3 is attached to the horn 15, the ultrasonic vibrations generated in the ultrasonic vibrator 12 are transmitted to a distal end from a proximal end in the probe 3. A length of the probe 3 along the longitudinal axis C is set so that the distal end of the probe 3 is located at an anti-node position of the ultrasonic vibrations. The ultrasonic vibrations are longitudinal vibrations in which a vibration transmission direction and a vibration direction are parallel to each other.

FIG. 4 is a diagram showing the configuration of a distal portion of the probe 3. As shown in FIG. 3 and FIG. 4, the probe 3 includes a distal surface portion 25. In the distal surface portion 25, an outer peripheral distal end P1 of the outer peripheral portion 21 is an outer edge. Cavitation is caused by the transmission of the ultrasonic vibrations to the distal surface portion 25. Living tissue, having low elasticity such as a hepatic cell, is shattered and resected by the cavitation. At the same time, elastic living tissue such as a blood vessel is not resected by the cavitation. As the distal end of the probe 3 is located at the anti-node position of the ultrasonic vibrations, the cavitation is more efficiently caused by the transmission of the ultrasonic vibrations to the distal surface portion 25.

When the probe 3 is attached to the horn 15, a probe-side current path of the high-frequency current is formed from the high-frequency current controller 9 to the distal portion of the probe 3 through the electric signal line 17, the ultrasonic vibrator 12, and the horn 15. Thus, the high-frequency current is transmitted between the high-frequency current controller 9 and the distal portion of the probe 3.

As shown in FIG. 3, a suction path 26 is formed inside the probe 3 from the proximal end to the distal end along the longitudinal axis C. That is, the probe 3 includes a path defining surface 27 which defines the suction path 26. When the probe 3 is attached to the horn 15, a proximal end of the suction path 26 is in communication with the space portion 19 provided inside the ultrasonic vibrator 12 and the horn 15.

As shown in FIG. 2, one end of a suction tube 28 is connected to the space portion 19. As shown in FIG. 1, the suction tube 28 extends to an outside of the vibrator case 11, and the other end of the suction tube 28 is connected to a suction unit 29. When suction substances such as the living tissue resected by the cavitation are suctioned, the suction unit 29 is driven, for example, by an input in the input unit 10. As the suction unit 29 is driven, the suction substances are suctioned from a distal end of the suction path 26. The suction substances are then suctioned to the suction unit 29 through the suction path 26, the space portion 19, and the suction tube 28 in order.

As shown in FIG. 1, the sheath unit 4 includes a sheath 31 through which the probe 3 is inserted, and the jaw 32 which is attached to a distal portion of the sheath 31. FIG. 5 is a diagram showing a state in which the probe 3 is inserted through the sheath 31. As shown in FIG. 5, the sheath 31 includes an outer pipe 33, and an inner pipe 35. A movable member 36 is provided between the outer pipe 33 and the inner pipe 35. The jaw 32 is attached to a distal portion of the outer pipe 33 via a linking screw 37.

A distal end of the movable member 36 is coupled to the jaw 32. The jaw 32 is rotated with respect to the sheath 31 around the linking screw 37 by the movement of the movable member 36 along the longitudinal axis C. In this way, the jaw 32 opens/closes with respect to the distal portion of the probe 3. As the jaw 32 opens/closes with respect to the distal portion of the probe 3, the living tissue, for example, can be held between the distal portion of the probe 3 and the jaw 32. Here, open/close directions (directions indicated by arrow A in FIG. 5) of the jaw 32 is perpendicular to the longitudinal axis C.

As shown in FIG. 5, a liquid supply path 38 is formed between the outer peripheral portion 21 of the probe 3 and the inner pipe 35 of the sheath 31 when the probe 3 is inserted through the sheath 31. That is, the liquid supply path 38 is defined by the outer peripheral portion 21 of the probe 3 and an inner peripheral surface of the inner pipe 35.

FIG. 6 is a schematic diagram showing the configuration of a coupling portion between the sheath 31 and the vibrator case 11. A distal portion of a cylindrical intermediary member 39 is attached to a proximal portion of the inner pipe 35 of the sheath 31. The sheath 31 is rotatable with respect to the intermediary member 39 around the longitudinal axis C. A distal portion of the vibrator case 11 is attached to a proximal portion of the intermediary member 39.

The liquid supply path 38 formed between the probe 3 and the sheath 31 extends to a distal face of the vibrator case 11. One end of a liquid supply tube 41 is connected to an inside of the intermediary member 39. As shown in FIG. 1, the liquid supply tube 41 extends to an outside of the handle unit 5, and the other end of the liquid supply tube 41 is connected to a liquid supply unit 43. The liquid supply unit 43 is connected to the input unit 10. When the liquid supply unit 43 is driven, for example, by an input in the input unit 10, a liquid passes through the liquid supply tube 41 and the liquid supply path 38 in order. The liquid is then supplied to the living tissue from a clearance between a distal end of the sheath 31 and the probe 3. In ultrasonic suction, a liquid such as a physiological saline solution is supplied to a vicinity of a treatment position from the liquid supply unit 43.

An electric signal line (not shown) extending from the high-frequency current controller 9 of the power supply unit 7 through the inside of the cable 6 is connected to the vibrator case 11. The vibrator case 11 and the intermediary member 39 include electrically conductive portions (not shown) which are electrically connect the electric signal line from the high-frequency current controller 9 to the sheath 31. Accordingly, a jaw-side current path is formed from the high-frequency current controller 9 to the jaw 32 through the electrically conductive portion of the vibrator case 11 and the sheath 31. The ultrasonic vibrator 12 and the horn 15 are insulated from the vibrator case 11.

As shown in FIG. 5, an insulating member 45 is attached to the outer peripheral portion 21 of the probe 3 by a rubber lining. The insulating member 45 is located at a node position of ultrasonic waves. The probe 3 is supported by the sheath 31 via the insulating member 45. By the provision of the insulating member 45, the contact between the probe 3 and the inner pipe 35 of the sheath 31 is prevented, and the probe 3 is insulated from the sheath 31. Insulating coating is preferably provided in the inner peripheral surface of the inner pipe 35. This more effectively prevents the electric conduction between the probe 3 and the sheath 31 via the liquid passing through the liquid supply path 38.

Figure 7:
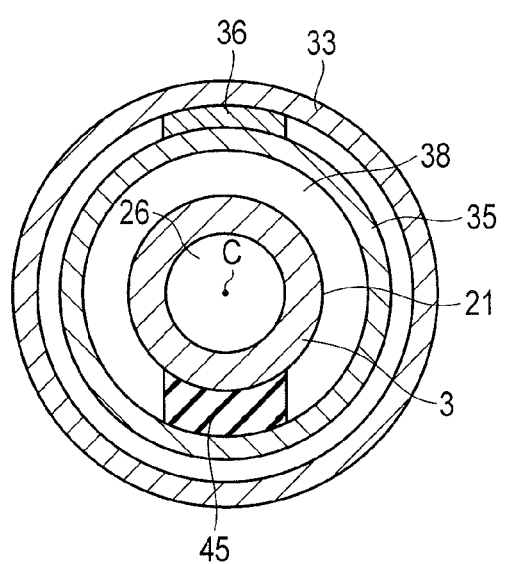
FIG. 7 is a sectional view taken along line VII-VII of FIG. 5.

FIG. 7 is a sectional view taken along line VII-VII of FIG. 5. As shown in FIG. 7, the insulating member 45 is only attached over a predetermined angular range of the outer peripheral portion 21 of the probe 3 in directions around the longitudinal axis C. That is, the insulating member 45 is not attached an all-round of the outer peripheral portion 21 of the probe 3. Therefore, the liquid can pass through a part where the insulating member 45 is located in directions parallel to the longitudinal axis C.

Figure 8:
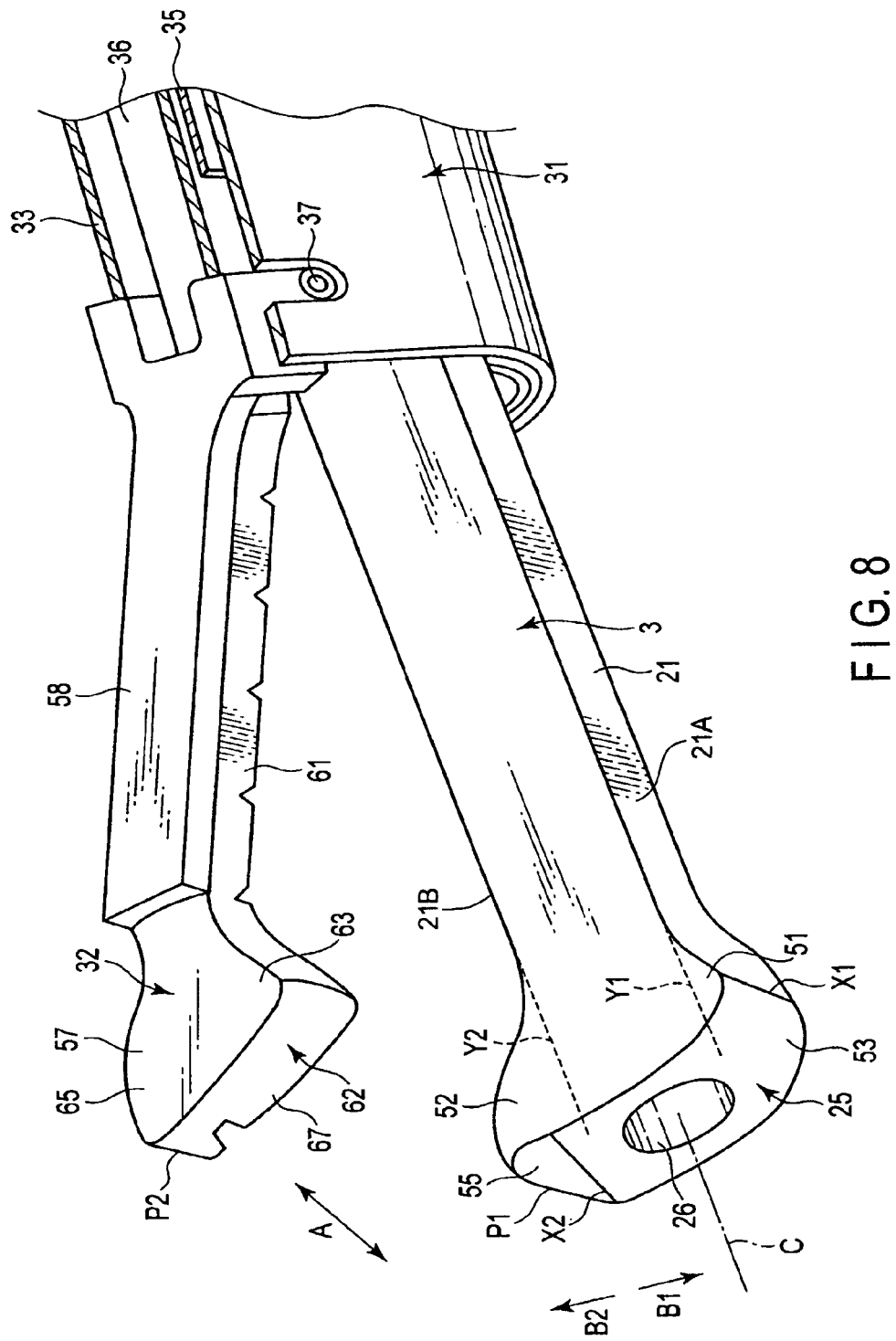
FIG. 8 is a schematic perspective view showing the distal portion of the probe and a jaw open with respect to the distal portion of the probe according to the first embodiment.

FIG. 8 is a diagram showing the distal portion of the probe 3 and the jaw 32 open with respect to the distal portion of the probe 3. As shown in FIG. 3, FIG. 4, and FIG. 8, the probe 3 includes a first protrusion 51 which protrudes the outer peripheral distal end P1 of the outer peripheral portion 21 toward a first perpendicular direction (direction indicated by arrow B1 in FIG. 3, FIG. 4, and FIG. 8), which is perpendicular to the longitudinal axis C and perpendicular to the open/close directions (directions indicated by arrow A in FIG. 4 and FIG. 8) of the jaw 32. The probe 3 also includes a second protrusion 52 which protrudes the outer peripheral distal end P1 of the outer peripheral portion 21 toward a second perpendicular direction (direction indicated by arrow B2 in FIG. 3, FIG. 4, and FIG. 8), which is opposite to the first perpendicular direction.

The distal surface portion 25 of the probe 3 includes an inclined plane 53 in which it goes toward the distal direction side as it goes from the first perpendicular direction toward the second perpendicular direction. The inclined plane 53 extends from a first end position X1 to a second end position X2. The first end position X1 of the inclined plane 53 corresponds to an end of the outer peripheral distal end P1 of the outer peripheral portion 21 on the first perpendicular direction side. That is, the first end position X1 of the inclined plane 53 is located to the first perpendicular direction side of a first root position Y1, which is a root position of the first protrusion 51. The second end position X2 of the inclined plane 53 is located to the second perpendicular direction side of a second root position Y2, which is a root position of the second protrusion 52. That is, the second end position X2 of the inclined plane 53 is located to the second perpendicular direction side of the suction path 26. As described above, in the distal surface portion 25 including the inclined plane 53, the outer peripheral distal end P1 of the outer peripheral portion 21 is an outer edge. Thus, in a part of the outer peripheral distal end P1 of the outer peripheral portion 21 serving as an outer edge of the inclined plane 53, it goes toward the distal directions side as it goes from the first perpendicular direction toward the second perpendicular direction.

The distal surface portion 25 includes a curved surface 55 provided to the second perpendicular direction side of the inclined plane 53. The curved surface 55 extends from the second end position X2 to an end of the outer peripheral distal end P1 of the outer peripheral portion 21 on the second perpendicular direction side. In the curved surface 55, it goes toward the proximal direction side as it goes from the first perpendicular direction toward the second perpendicular direction.

Figure 9:
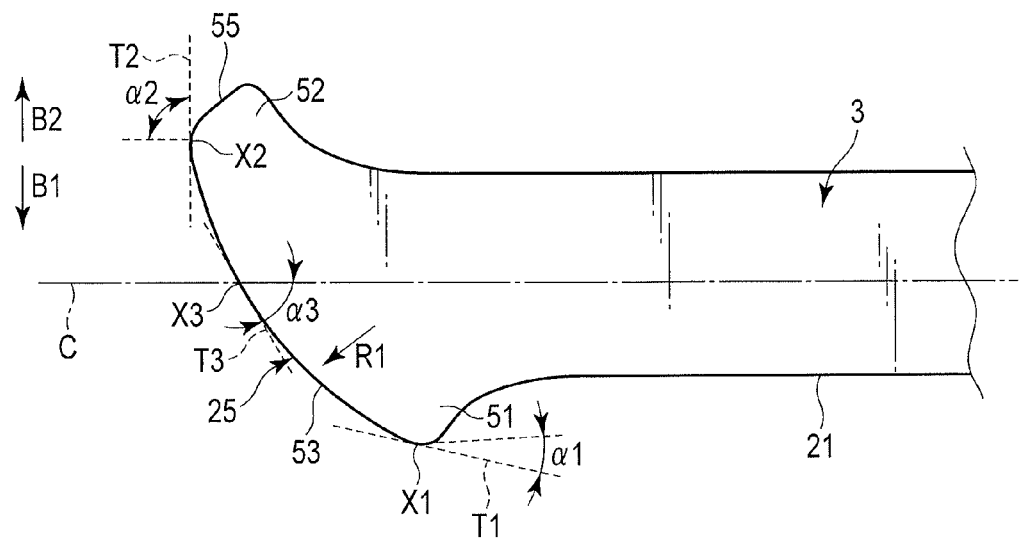
FIG. 9 is a schematic diagram showing the distal portion of the probe according to the first embodiment when viewed from one of open/close directions of the jaw.

FIG. 9 is a diagram showing the probe 3 when viewed from one of the open/close directions of the jaw 32. As shown in FIG. 9, the inclined plane 53 of the distal surface portion 25 is an arc-shaped curved surface having a constant curvature R1 when viewed from one of the open/close directions of the jaw 32. In the inclined plane 53, acute angles (α1 to α3) between tangential lines (T1 to T3) of the inclined plane 53 and the longitudinal axis C increase as it goes from the first perpendicular direction (direction indicated by arrow B1 in FIG. 9) toward the second perpendicular direction (direction indicated by arrow B2 in FIG. 9) when viewed from one of the open/close directions of the jaw 32. Here, tangential line T1 is tangent to the inclined plane 53 at the first end position X1, and tangential line T2 is tangent to the inclined plane 53 at the second end position X2. Tangential line T3 is tangent to the inclined plane 53 at a position X3 between the first end position X1 and the second end position X2. In this case, acute angle α3 between tangential line T3 and the longitudinal axis C is greater than acute angle α1 between tangential line T1 and the longitudinal axis C. Acute angle α2 between tangential line T2 and the longitudinal axis C is greater than acute angle α3 between tangential line T3 and the longitudinal axis C. Acute angle α2 between tangential line T2 and the longitudinal axis C is preferably greater than 70° at the second end position X2 of the inclined plane 53.

Figure 10:
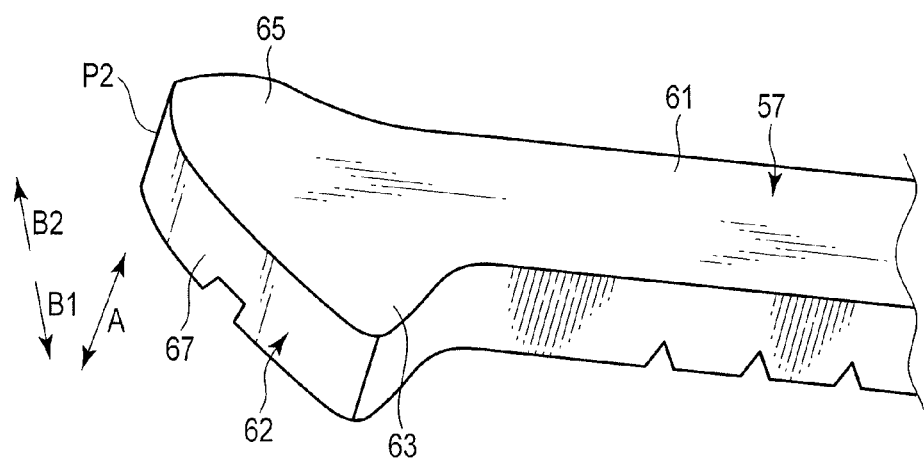
FIG. 10 is a schematic perspective view showing the configuration of a jaw body of the jaw according to the first embodiment.

As shown in FIG. 8, the jaw 32 includes a jaw body 57, and a coupling member 58 which couples the jaw body 57 to the sheath 31. FIG. 10 is a diagram showing the configuration of the jaw body 57. As shown in FIG. 8 and FIG. 10, the jaw body 57 (jaw 32) includes a jaw-side outer peripheral portion 61. The jaw-side outer peripheral portion 61 is provided along the longitudinal axis C when the jaw 32 is closed with respect to the distal portion of the probe 3. The jaw body 57 (jaw 32) includes a jaw-side distal surface portion 62 in which an outer peripheral distal end P2 of the jaw-side outer peripheral portion 61 is an outer edge.

The jaw body 57 includes a first jaw-side protrusion 63 which protrudes the outer peripheral distal end P2 of the jaw-side outer peripheral portion 61 toward the first perpendicular direction (direction indicated by arrow B1 in FIG. 10), which is perpendicular to the longitudinal axis C and perpendicular to the open/close directions (directions indicated by arrow A in FIG. 10) of the jaw 32. The jaw body 57 also include a second jaw-side protrusion 65 which protrudes the outer peripheral distal end P2 of the jaw-side outer peripheral portion 61 toward the second perpendicular direction (direction indicated by arrow B2 in FIG. 10), which is opposite to the first perpendicular direction.

The jaw-side distal surface portion 62 includes a jaw-side inclined plane 67 in which it goes toward the distal direction side as it goes from the first perpendicular direction to the second perpendicular direction. As described above, in the jaw-side distal surface portion 62 including the jaw-side inclined plane 67, the outer peripheral distal end P2 of the jaw-side outer peripheral portion 61 is the outer edge. Thus, a part of the outer peripheral distal end P2 of the jaw-side outer peripheral portion 61 serving as an outer edge of the jaw-side inclined plane 67, it goes toward the distal direction side as it goes from the first perpendicular direction toward the second perpendicular direction.

Figure 11:
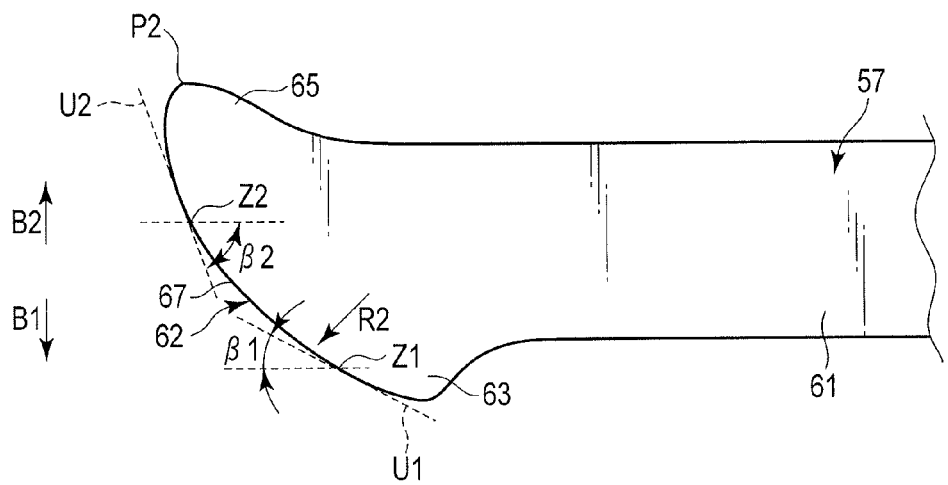
FIG. 11 is a schematic diagram showing the jaw body of the jaw according to the first embodiment when viewed from one of the open/close directions of the jaw.

FIG. 11 is a diagram showing the jaw body 57 when viewed from one of the open/close directions of the jaw 32. As shown in FIG. 11, the jaw-side inclined plane 67 of the jaw-side distal surface portion 62 is an arc-shaped jaw-side curved surface having a constant curvature R2 when viewed from one of the open/close directions of the jaw 32. Here, curvature R2 of the jaw-side inclined plane 67 is substantially the same as curvature R1 of the inclined plane 53 of the probe 3. In the jaw-side inclined plane 67, acute angles (β1 and β2) between the tangential lines (U1 and U2) of the jaw-side inclined plane 67 and the longitudinal axis C increase as it goes from the first perpendicular direction (direction indicated by arrow B1 in FIG. 11) toward the second perpendicular direction (direction indicated by arrow B2 in FIG. 11) when viewed from one of the open/close directions of the jaw 32. Here, tangential line U1 is tangent to the jaw-side inclined plane 67 at a position Z1, and tangential line U2 is tangent to the jaw-side inclined plane 67 at a position Z2 located to the second perpendicular direction side of the position Z1. In this case, acute angle β2 between tangential line U2 and the longitudinal axis C is greater than acute angle β1 between tangential line U1 and the longitudinal axis C. As described above, the jaw-side inclined plane 67 is formed into a shape corresponding to the inclined plane 53 of the probe 3.

As shown in FIG. 1, the handle unit 5 includes a cylindrical case 71, a fixed handle 72 provided integrally with the cylindrical case 71, and a movable handle 73 configured to open/close with respect to the fixed handle 72. The cylindrical case 71 is attached to the vibrator case 11, and is made of an insulating material. The movable handle 73 is coupled, via an intermediary member (not shown), to the movable member 36 provided in the sheath 31. The movable handle 73 is opened/closed with respect to the fixed handle 72, and the movable member 36 thereby moves along the longitudinal axis C. Thus, the jaw 32 opens/closes with respect to the distal portion of the probe 3.

Two operation buttons 75A and 75B are provided in the fixed handle 72. The operation buttons 75A and 75B are electrically connected to the power supply unit 7, for example, via electric signal line (not shown) passing through the inside of the cable 6. The ultrasonic controller 8 and the high-frequency current controller 9 of the power supply unit 7 is configured to control whether to output a current and configured to control an intensity of the current to be output, in accordance with operation states in the operation buttons 75A and 75B. An operator selectively presses the operation buttons 75A and 75B to suit to a treatment. For example, when the operator presses the operation button 75A, a current is only output from the ultrasonic controller 8. As a result, ultrasonic vibrations are generated in the ultrasonic vibrator 12, and the ultrasonic vibrations are transmitted to the distal end of the probe 3. In this case, no high-frequency current flows through the probe-side current path and the jaw-side current path. In contrast, when the operator presses the operation button 75B, a current is only output from the high-frequency current controller 9. As a result, a high-frequency current flows through the probe-side current path and the jaw-side current path. In this case, no ultrasonic vibrations are generated.

A rotational operation knob 77 is coupled to the distal direction side of the cylindrical case 71. The rotational operation knob 77 is rotatable with respect to the cylindrical case 71 around the longitudinal axis C. The rotational operation knob 77 is made of an insulating material. The sheath 31 is attached to an inner peripheral side of the rotational operation knob 77. If the rotational operation knob 77 is rotated, the probe 3, the sheath 31, and the jaw 32 rotate around the longitudinal axis C together with the rotational operation knob 77.

Figure 12:
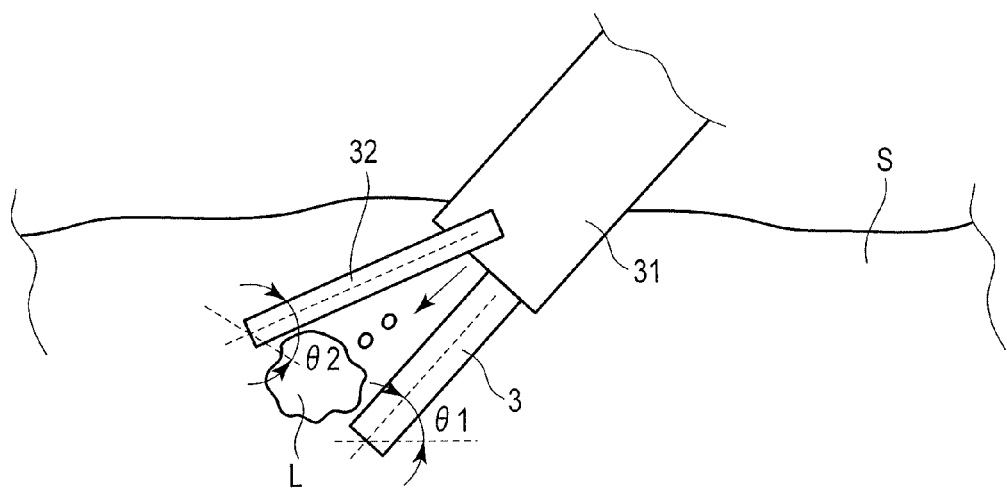
FIG. 12 is a schematic diagram showing a bipolar treatment performed while the jaw is open with respect to the probe according to the first embodiment.

Now, the functions of the bipolar treatment device 1 are described. FIG. 12 is a diagram showing a bipolar treatment performed while the jaw 32 is open with respect to the probe 3. As shown in FIG. 12, to perform a bipolar treatment while the jaw 32 is open with respect to the probe 3, the movable handle 73 is opened with respect to the fixed handle 72 so that the jaw 32 is open with respect to the probe 3. In this condition, the probe 3 and the jaw 32 are brought into contact with living tissue S.

FIG. 13A is a diagram showing the contact between the probe 3 and the living tissue S in the bipolar treatment performed while the jaw 32 is open with respect to the probe 3. FIG. 13B is a diagram showing the contact between the jaw 32 and the living tissue S in the bipolar treatment performed while the jaw 32 is open with respect to the probe 3. When the probe 3 and the jaw 32 are in contact with the living tissue S, the probe 3 is in surface contact with the living tissue S in the inclined plane 53 of the distal surface portion 25, as shown in FIG. 13A. The jaw 32 is in surface contact with the living tissue S in the jaw-side inclined plane 67 of the jaw-side distal surface portion 62, as shown in FIG. 13B. An angle θ1 between the probe 3 and the living tissue S and an angle θ2 between the jaw 32 and the living tissue S are generally about 30 to 80°. This ensures visibility during a treatment and operability when the fixed handle 72 and the movable handle 73 are held.

If the liquid supply unit 43 is driven, for example, by an input in the input unit 10, a given amount of a liquid L such as a physiological saline solution is supplied from the distal end of the liquid supply path 38. The liquid L is supplied to a part of the surface of the living tissue S located between the jaw 32 and the probe 3. In this condition, if the operation button 75B is pressed, a high-frequency current flows to the probe-side current path and the jaw-side current path from the high-frequency current controller 9. As a result, the high-frequency current flows through the living tissue S between the jaw 32 and the probe 3 via the supplied liquid L. The living tissue S is reformed by the high-frequency current, and is coagulated. In this way, the living tissue S is coagulated over a wide range between the jaw 32 opened with respect to the probe 3 and the probe 3.

Here, in the bipolar treatment performed by dropping the physiological saline solution while the jaw 32 is open with respect to the probe 3, the physiological saline solution is dropped between the jaw 32 opened with respect to the probe 3 and the probe 3. The physiological saline solution is then boiled by the high-frequency current from the probe 3 and the jaw 32, and the living tissue S is thereby treated over a wide range. It is therefore necessary to ensure the area of contact between the probe 3 and the living tissue S and the area of contact between the jaw 32 and the living tissue S that are required to boil, over a wide range, the physiological saline solution dropped between the jaw 32 and the probe 3. In the present embodiment, the probe 3 is in surface contact with the living tissue S with a suitable magnitude (about 30 to 80°) of angle θ1 between the probe 3 and the living tissue S, as shown in FIG. 13A. The jaw 32 is also in surface contact with the living tissue S with a suitable magnitude (about 30 to 80°) of angle θ2 between the jaw 32 and the living tissue S, as shown in FIG. 13B. Thus, the high-frequency current efficiently flows through the living tissue S over a wide range between the jaw 32 and the probe 3, and the living tissue S is efficiently coagulated.

Figure 14B:
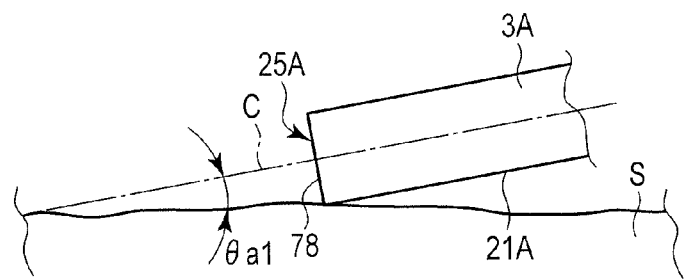
FIG. 14B is a schematic diagram showing a state in which the probe is in contact with the living tissue when an angle between the probe and the living tissue is smaller than the angle in FIG. 14A according to the first comparative example of the first embodiment.

Suppose a probe 3A without the inclined plane 53 as a first comparative example, as shown in FIG. 14A and FIG. 14B. In the probe 3A, a distal surface portion 25A is only formed by a perpendicular plane 78 perpendicular to the longitudinal axis C. The probe 3A does not include the inclined plane 53. Thus, as shown in FIG. 14A, the probe 3A is not in surface contact with the living tissue S but is in point contact or line contact with the living tissue S with a suitable magnitude (about 30 to 80°) of an angle θa1 between the probe 3A and the living tissue S, as shown in FIG. 14A. This does not ensure the area of contact between the probe 3A and the living tissue S that is required to boil the physiological saline solution dropped on the living tissue S over a wide range between the jaw 32 and the probe 3A.

As shown in FIG. 14B, it is possible to bring the outer peripheral portion 21A of the probe 3A into surface contact with the living tissue S by reducing angle θa1 between the probe 3A and the living tissue S to almost zero. However, if angle θa1 between the probe 3A and the living tissue S is almost zero, the probe 3A tends to contact the living tissue S in parts to the proximal direction side of a part where the outer peripheral portion 21A of the probe 3A is in surface contact with the living tissue S. Therefore, the high-frequency current may flow through parts other than the physiological saline solution dropped between the jaw 32 and the part where the outer peripheral portion 21A of the probe 3A is in surface contact with the living tissue S. As a result, the performance of the bipolar treatment deteriorates. Moreover, as angle θa1 between the probe 3A and the living tissue S is not a suitable magnitude of about 30 to 80°, visibility during a treatment and operability when the fixed handle 72 and the movable handle 73 are held deteriorate.

In the meantime, the probe 3 according to the present embodiment is provided with the inclined plane 53 in the distal surface portion 25. Therefore, the probe 3 comes into surface contact with the living tissue S with a general magnitude (about 30 to 80°) of angle θ1 between the probe 3 and the living tissue S. This ensures the area of contact between the probe 3 and the living tissue S that is required to pass the high-frequency current through the physiological saline solution dropped on the living tissue S over a wide range between the jaw 32 and the probe 3.

Similarly, the jaw 32 is provided with the jaw-side inclined plane 67 in the jaw-side distal surface portion 62. Therefore, the jaw 32 comes into surface contact with the living tissue S with a suitable magnitude (about 30 to 80°) of angle θ2 between the jaw 32 and the living tissue S. This ensures the area of contact between the jaw 32 and the living tissue S that is required to pass the high-frequency current through the physiological saline solution dropped on the living tissue S over the wide range between the jaw 32 and the probe 3. Consequently, by the provision of the inclined plane 53 and the jaw-side inclined plane 67, the high-frequency current efficiently flows through the physiological saline solution dropped on the living tissue S over the wide range between the jaw 32 and the probe 3 with a suitable magnitude of angle θ1 between the probe 3 and the living tissue S and with a suitable magnitude of angle θ2 between the jaw 32 and the living tissue S. Therefore, the living tissue S is efficiently coagulated.

Figure 15:
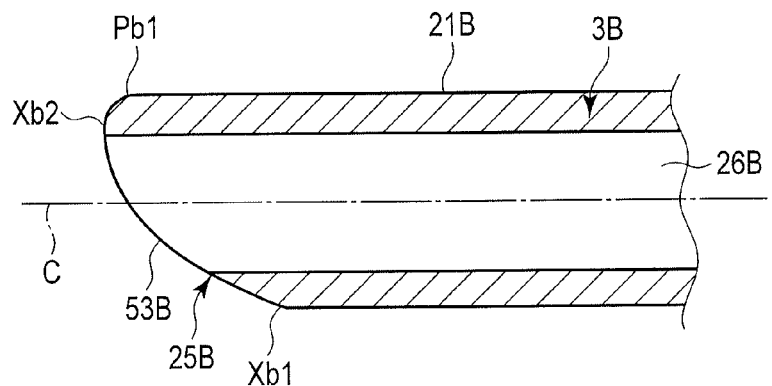
FIG. 15 is a schematic sectional view showing the configuration of a distal portion of a probe according a second comparative example of the first embodiment.

In the bipolar treatment device 1 having the ultrasonic suction function according to the present embodiment, the suction path 26 is formed in the probe 3. Here, suppose a probe 3B without the first protrusion 51 and the second protrusion 52 as a second comparative example, as shown in FIG. 15. A distal surface portion 25B of the probe 3B includes an inclined plane 53B extending from a first end position Xb1 to a second end position Xb2. As the inclined plane 53 according to the first embodiment, in the inclined plane 53B, it goes toward the distal direction side, as it goes from the first perpendicular direction toward the second perpendicular direction. The first end position Xb1 of the inclined plane 53B corresponds to an end of an outer peripheral distal end Pb1 of an outer peripheral portion 21B on the first perpendicular direction side. The second end position Xb2 of the inclined plane 53B is located to the second perpendicular direction side of a suction path 26B.

In the probe 3B, the suction path 26B extends to the distal surface portion 25B, and a surface area of the inclined plane 53B is thereby reduced. In the bipolar treatment performed while the jaw 32 is open with respect to the probe 3B, the probe 3B can be more easily brought into surface contact with the living tissue S with a general magnitude (about 30 to 80°) of an angle θb1 between the probe 3B and the living tissue S when the surface area of the inclined plane 53B is greater. It is indeed possible to increase the surface area of the inclined plane 53B by making the probe 3B thicker in a state that a sectional area of the suction path 26B perpendicular to the longitudinal axis C remains the same. However, if the probe 3B is thicker, the probe 3B is increased in size and weight, and the movement of the probe 3B, for example, becomes difficult. Accordingly, operability at the time of a treatment deteriorates.

In the meantime, the probe 3 according to the present embodiment includes the first protrusion 51 which protrudes the outer peripheral distal end P1 of the outer peripheral portion 21 toward the first perpendicular direction. The first end position X1 of the inclined plane 53 is located to the first perpendicular direction side of the first root position Y1 of the first protrusion 51. The second end position X2 of the inclined plane 53 is located to the second perpendicular direction side of the suction path 26. Such a configuration allows the surface area of the inclined plane 53 to be increased without the increase of the probe 3 in size and weight even when the suction path 26 is provided inside. Therefore, even when the suction path 26 is provided, the probe 3 can be easily brought into surface contact with the living tissue S with a suitable magnitude (about 30 to 80°) of angle θ1 between the probe 3 and the living tissue S.

The probe 3 also includes the second protrusion 52 which protrudes the outer peripheral distal end P1 of the outer peripheral portion 21 toward the second perpendicular direction. The second end position X2 of the inclined plane 53 is located to the second perpendicular direction side of the second root position Y2 of the second protrusion 52. This allows the surface area of the inclined plane 53 to be further increased. Therefore, the probe 3 can be more easily brought into surface contact with the living tissue S with a suitable magnitude of angle θ1 between the probe 3 and the living tissue S.

Furthermore, in the probe 3, the first end position X1 of the inclined plane 53 corresponds to the end of the outer peripheral distal end P1 of the outer peripheral portion 21 on the first perpendicular direction side. Thus, the surface area of the inclined plane 53 is greater. Consequently, the probe 3 can be more easily brought into surface contact with the living tissue S with a suitable magnitude of angle θ1 between the probe 3 and the living tissue S.

Figure 16:
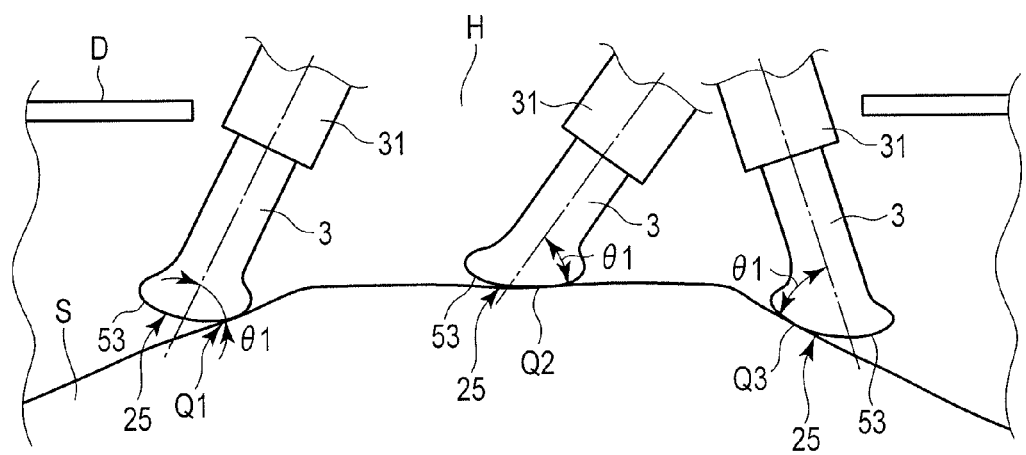
FIG. 16 is a schematic diagram showing the contact between the probe and the living tissue at various positions of the living tissue when the bipolar treatment is performed while the jaw is open with respect to the probe according to the first embodiment.

FIG. 16 is a diagram showing the contact between the probe 3 and the living tissue S at various positions of the living tissue S when the bipolar treatment is performed while the jaw 32 is open with respect to the probe 32. As shown in FIG. 16, when a bipolar treatment is performed, a hole H is made in a body wall D, and the probe 3 is inserted into a body cavity from the hole H. Here, the inclined plane 53 of the distal surface portion 25 is an arc-shaped curved surface having a constant curvature R1 when viewed from one of the open/close directions of the jaw 32. In the inclined plane 53, the acute angles ($\alpha 1$ to $\alpha 3$) between the tangential lines (T1 to T3) of the inclined plane 53 and the longitudinal axis C increase as it goes from the first perpendicular direction toward the second perpendicular direction when viewed from one of the open/close directions of the jaw 32. Such a configuration of the inclined plane 53 allows a greater range in which the probe 3 can be in surface contact with the living tissue S with a suitable magnitude (about 30 to 80°) of angle θ1 between the probe 3 and the living tissue S. For example, at all positions Q1 to Q3 of the living tissue S, the probe 3 can be in surface contact with the living tissue S with a suitable magnitude of angle θ1 between the probe 3 and the living tissue S. Therefore, bipolar treatments can be performed at various positions of the living tissue S by making one hole H in the body wall D.

The jaw-side inclined plane 67 of the jaw-side distal surface portion 62 is the arc-shaped jaw-side curved surface having the constant curvature R2 when viewed from one of the open/close directions of the jaw 32. In the jaw-side inclined plane 67, the acute angles ($\beta 1$ and $\beta 2$) between the tangential lines (U1 and U2) of the jaw-side inclined plane 67 and the longitudinal axis C increase as it goes from the first perpendicular direction toward the second perpendicular direction when viewed from one of the open/close directions of the jaw 32. Such a configuration of the jaw-side inclined plane 67 allows a greater range in which the jaw 32 can be in surface contact with the living tissue S with a suitable magnitude (about 30 to 80°) of angle $\theta 2$ between the jaw 32 and the living tissue S. Therefore, bipolar treatments can be performed at various positions of the living tissue S by making one hole H in the body wall D.

Curvature R2 of the jaw-side inclined plane 67 is substantially the same as curvature R1 of the inclined plane 53 of the probe 3 when viewed from one of the open/close directions of the jaw 32. That is, the jaw-side inclined plane 67 is formed into a shape corresponding to the inclined plane 53 of the probe 3. It is thus easier to bring the probe 3 into surface contact with the living tissue S with a suitable magnitude of angle $\theta 1$ between the probe 3 and the living tissue S, and to also bring the jaw 32 into surface contact with the living tissue S with a suitable magnitude of angle $\theta 2$ between the jaw 32 and the living tissue S simultaneously. Accordingly, operability at the time of a bipolar treatment is improved.

When the ultrasonic suction is performed, the operation button 75A is first pressed, and a current is output from the ultrasonic controller 8. As a result, ultrasonic vibrations are generated in the ultrasonic vibrator 12, and the ultrasonic vibrations are transmitted to the distal surface portion 25 of the probe 3. In the meantime, a liquid such as a physiological saline solution is supplied to the vicinity of a treatment position from the liquid supply unit 43. Cavitation is caused by the transmission of the ultrasonic vibrations to the distal surface portion 25 while the liquid is being supplied. Living tissue having low elasticity such as a hepatic cell is selectively shattered and resected by the cavitation. The suction unit 29 is then driven, for example, by an input in the input unit 10, and the living tissue resected by the cavitation is suctioned from the distal end of the suction path 26. The suction substances are then suctioned to the suction unit 29 through the suction path 26, the space portion 19, and the suction tube 28 in order. In this case, a liquid such as a physiological saline solution supplied from the liquid supply unit 43 to generate cavities and clean the inside of the body cavity is supplied to the living tissue from a distal end of the liquid supply path 38.

Figure 17:
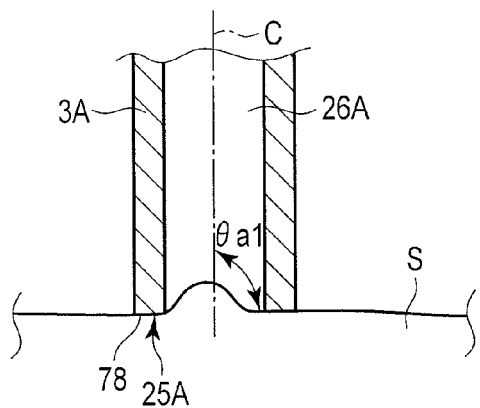
FIG. 17 is a schematic diagram showing a state in which ultrasonic suction is performed by the probe according to the first comparative example of the first embodiment.

Here, suppose that ultrasonic suction is performed by the probe 3A of the first comparative example shown in FIG. 14A and FIG. 14B. FIG. 17 is a diagram showing a state in which the ultrasonic suction is performed by the probe 3A. As shown in FIG. 17, when the ultrasonic suction is performed, it is suitable that a angle $\theta a1$ between the probe 3A and the living tissue S make a substantially right angle to efficiently cause cavitation. In the probe 3A, the distal surface portion 25A is only formed by the perpendicular plane 78 perpendicular to the longitudinal axis C. The distal end of a suction path 26A extends to the perpendicular plane 78. Thus, an opening at the distal end of the suction path 26A is formed to be perpendicular to the longitudinal axis C.

The living tissue is resected by the cavitation while the perpendicular plane 78 is almost in contact with the living tissue S. Here, when suction from the opening of the suction path 26A is performed at the same time, the living tissue or the like that is not shattered by the cavitation tends to adhere to the opening. The stability of the suction deteriorates because of the adhesion of the unshattered living tissue to the opening.

Figure 18:
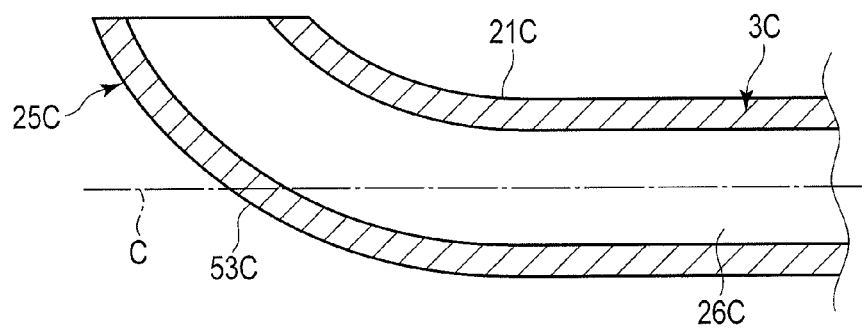
FIG. 18 is a schematic sectional view showing the configuration of a distal portion of a probe according a third comparative example of the first embodiment.

Suppose, as a third comparative example, a probe 3C in which an opening at the distal end of a suction path 26C is provided in an outer peripheral portion 21C, as shown in FIG. 18. A distal surface portion 25C of the probe 3C includes an inclined plane 53C. As the inclined plane 53 according to the first embodiment, in the inclined plane 53C, it goes to the distal direction side as it from the first perpendicular direction toward the second perpendicular direction. In the probe 3C, the suction path 26C is curved from the first perpendicular direction to the second perpendicular direction. Thus, an opening direction at the distal end of the suction path 26C is not parallel to the longitudinal axis C.

In the probe 3C, the distal end of the suction path 26C does not extend to the distal surface portion 25C. Thus, the inclined plane 53C can be formed to be a continuous surface, and the surface area of the inclined plane 53C can be increased without the increase of the probe 3C in size and weight. Therefore, the probe 3C can be easily brought into surface contact with the living tissue S with a suitable magnitude (about 30 to 80°) of an angle $\theta c1$ between the probe 3C and the living tissue S.

However, during ultrasonic suction, a liquid such as water is supplied from the distal end of the liquid supply path 38 to cause cavitation and clean the inside of the body cavity. The liquid supplied from the distal end of the liquid supply path 38 passes through a part of the outer peripheral portion 21C of the probe 3C located to the distal direction side of the sheath 31. Thus, when the opening direction at the distal end of the suction path 26C is configured not to be parallel to the longitudinal axis C, the liquid supplied from the liquid supply path 38 is easily suctioned into the suction path 26C. As a result, the stability of the liquid supply deteriorates.

Figure 19:
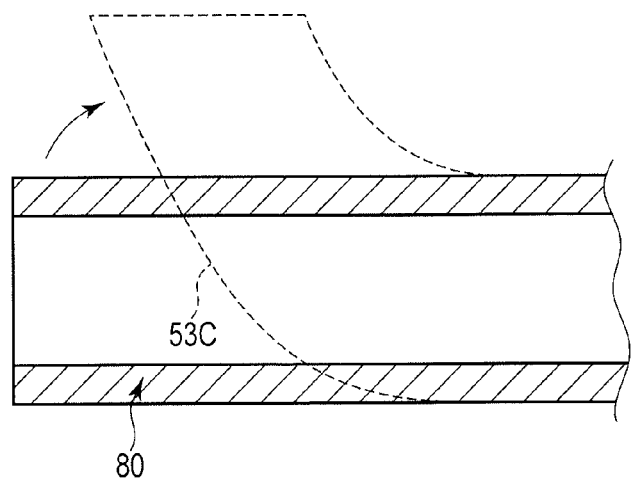
FIG. 19 is a schematic diagram showing a method of manufacturing the probe according the third comparative example of the first embodiment.

FIG. 19 is a diagram illustrating a method of manufacturing the probe 3C according to the third comparative example. As shown in FIG. 19, when the probe 3C is manufactured, a linear cylindrical member 80 is formed, for example, by perforation. The cylindrical member 80 is then curved from the first perpendicular direction to the second perpendicular direction, for example, by bending, and the inclined plane 53C is thereby formed. The probe 3C is then formed by milling. However, the operation of bending the cylindrical member 80 is complicated. This leads to higher costs and longer working time.

In the probe 3C, the suction path 26C is curved by bending. The resected living tissue or the like tends to be retained in a curved part of the suction path 26C, and the stability of suction deteriorates. As the distal end of the suction path 26C is provided in the outer peripheral portion 21C in the probe 3C, the opening direction at the distal end of the suction path 26C is not parallel to the longitudinal axis C. In the ultrasonic suction device (1) generally used by the operator, an opening direction at a distal end of a suction path (26) is parallel to the longitudinal axis C, as in the probe 3 according to the present embodiment. Thus, it is difficult for the operator to perform the ultrasonic suction treatment with the probe 3C in which the opening direction at the distal end of the suction path 26C is not parallel to the longitudinal axis C. Therefore, the working efficiency at the time of the ultrasonic suction deteriorates.

The use of the probe 3C for a long time induces stress release, and the probe 3C is restored to its original shape in a part curved by bending. Accordingly, the probe 3C is deformed. This changes the abutment between the probe 3C and the jaw 32, and deteriorates the performance of holding the living tissue or the like between the probe 3C and the jaw 32.

In the meantime, in the probe 3 according to the present embodiment, the suction path 26 is formed to extend to the distal surface portion 25 along the longitudinal axis C. The opening direction at the distal end of the suction path 26 is parallel to the longitudinal axis C. Thus, it is easy for the operator to perform the ultrasonic suction treatment. The probe 3 can only be manufactured by perforation and milling, and bending is not needed to manufacture the probe 3. Therefore, the probe 3 can be easily manufactured with low costs. As bending is not performed to manufacture the probe 3, the probe 3 is not deformed by force that brings back to the original shape, even when used for a long time.

In the probe 3, the suction path 26 extends to the distal surface portion 25, and the opening direction at the distal end of the suction path 26 is parallel to the longitudinal axis C. Thus, the liquid supplied from the liquid supply path 38 is not easily suctioned into the suction path 26C. Therefore, the liquid is stably supplied in the ultrasonic suction treatment.

According to the present embodiment, in the inclined plane 53 of the probe 3, it goes toward the distal direction side as it goes from the first perpendicular direction toward the second perpendicular direction. The first end position X1 of the inclined plane 53 is located to the first perpendicular direction side of the first root position Y1 of the first protrusion 51. The second end position X2 of the inclined plane 53 is located to the second perpendicular direction side of the suction path 26. In such a configuration, in the opening at the distal end of the suction path 26 is formed so that it goes toward the distal direction side as it goes from the first perpendicular direction toward the second perpendicular direction.

FIG. 20 is a diagram showing a state in which ultrasonic suction is performed by the probe 3. As shown in FIG. 20, when the ultrasonic suction is performed, an angle θ1 between the probe 3 and the living tissue S make a substantially right angle, and the distal surface portion 25 is almost in contact with the living tissue S. In the opening at the distal end of the suction path 26 in the probe 3, it goes toward the distal direction side as it goes from the first perpendicular direction toward the second perpendicular direction. Thus, even when suction from the opening of the suction path 26 is performed at the same time, the living tissue or the like that is not shattered by the cavitation does not easily adhere to the opening. As the suction path 26 is not curved, the living tissue or the like is not easily retained in the suction path 26. Therefore, the suction is stably performed in the ultrasonic suction.

The inclined plane 53 of the distal surface portion 25 is an arc-shaped curved surface having the constant curvature R1 when viewed from one of the open/close directions of the jaw 32. In the inclined plane 53, the acute angles (α1 to α3) between the tangential lines (T1 to T3) of the inclined plane 53 and the longitudinal axis C increase as it goes from the first perpendicular direction toward the second perpendicular direction when viewed from one of the open/close directions of the jaw 32. In the distal surface portion 25, cavitation is more efficiently caused by ultrasonic vibrations in parts where the acute angles (α1 to α3) between the tangential lines (T1 to T3) of the distal surface portion 25 (inclined plane 53) and the longitudinal axis C are greater when viewed from one of the open/close directions of the jaw 32. In the probe 3, the second end position X2 of the inclined plane 53 is located to the second perpendicular direction side of the second root position Y2 of the second protrusion 52. Thus, in the part of the inclined plane 53 on the second perpendicular direction side, the acute angles (α1 to α3) between the tangential lines (T1 to T3) of the inclined plane 53 and the longitudinal axis C are greater when viewed from one of the open/close directions of the jaw 32. As a result, in the part of the inclined plane 53 on the second perpendicular direction side, cavitation is more efficiently caused by ultrasonic vibrations. Therefore, the living tissue is efficiently and safely resected in the ultrasonic suction.

Acute angle α2 between tangential line T2 at the second end position X2 of the inclined plane 53 and the longitudinal axis C is preferably greater than 70° when viewed from one of the open/close directions of the jaw 32. Thus, in the part of the inclined plane 53 on the second perpendicular direction side, the acute angles (α1 to α3) between the tangential lines (T1 to T3) of the inclined plane 53 and the longitudinal axis C are greater when viewed from one of the open/close directions of the jaw 32. As a result, in the part of the inclined plane 53 on the second perpendicular direction side, cavitation is more efficiently caused by ultrasonic vibrations.

Accordingly, the bipolar treatment device 1 having the configuration described above has the following advantages. That is, in the bipolar treatment device 1 according to the present embodiment, the inclined plane 53 is provided in the distal surface portion 25. Therefore, the probe 3 comes into surface contact with the living tissue S with a suitable magnitude (about 30 to 80°) of angle θ1 between the probe 3 and the living tissue S. This can ensure the area of contact between the probe 3 and the living tissue S that is required to pass the high-frequency current through the physiological saline solution dropped on the living tissue S over a wide range between the jaw 32 and the probe 3.

Similarly, in the jaw 32, the jaw-side inclined plane 67 is provided in the jaw-side distal surface portion 62. Therefore, the jaw 32 comes into surface contact with the living tissue S with a suitable magnitude (about 30 to 80°) of angle θ2 between the jaw 32 and the living tissue S. This can ensure the area of contact between the jaw 32 and the living tissue S that is required to pass the high-frequency current through the physiological saline solution dropped on the living tissue S over the wide range between the jaw 32 and the probe 3. Consequently, by the provision of the inclined plane 53 and the jaw-side inclined plane 67, the high-frequency current efficiently flows through the physiological saline solution dropped on the living tissue S over the wide range between the jaw 32 and the probe 3 with a suitable magnitude of angle θ1 between the probe 3 and the living tissue S and with a suitable magnitude of angle θ2 between the jaw 32 and the living tissue S. Therefore, the living tissue S can be efficiently coagulated in the bipolar treatment which uses, as electrodes, the jaw 32 opened with respect to the probe 3 and the probe 3, and which is performed by dropping the physiological saline solution.

In the bipolar treatment device 1, the probe 3 includes the first protrusion 51 which protrudes the outer peripheral distal end P1 of the outer peripheral portion 21 toward the first perpendicular direction. The first end position X1 of the inclined plane 53 is located to the first perpendicular direction side of the first root position Y1 of the first protrusion 51. The second end position X2 of the inclined plane 53 is located to the second perpendicular direction side of the suction path 26. Such a configuration allows the surface area of the inclined plane 53 to be increased without the increase of the probe 3 in size and weight even when the suction path 26 is provided inside. Therefore, even when the suction path 26 is provided, the probe 3 can be easily brought into surface contact with the living tissue S with a suitable magnitude (about 30 to 80°) of angle θ1 between the probe 3 and the living tissue S.

The probe 3 also includes the second protrusion 52 which protrudes the outer peripheral distal end P1 of the outer peripheral portion 21 toward the second perpendicular direction. The second end position X2 of the inclined plane 53 is located to the second perpendicular direction side of the second root position Y2 of the second protrusion 52. Moreover, in the probe 3, the first end position X1 of the inclined plane 53 corresponds to the end of the outer peripheral distal end P1 of the outer peripheral portion 21 on the first perpendicular direction side. Thus, the surface area of the inclined plane 53 can be greater. Consequently, the probe 3 can be more easily brought into surface contact with the living tissue S with a suitable magnitude of angle θ1 between the probe 3 and the living tissue S.

In the bipolar treatment device 1, the inclined plane 53 of the distal surface portion 25 is an arc-shaped curved surface having the constant curvature R1 when viewed from one of the open/close directions of the jaw 32. In the inclined plane 53, the acute angles (α1 to α3) between the tangential lines (T1 to T3) of the inclined plane 53 and the longitudinal axis C increase as it goes from the first perpendicular direction toward the second perpendicular direction when viewed from one of the open/close directions of the jaw 32. Such a configuration of the inclined plane 53 allows a greater range in which the probe 3 can be in surface contact with the living tissue S with a suitable magnitude (about 30 to 80°) of angle θ1 between the probe 3 and the living tissue S.

The jaw-side inclined plane 67 of the jaw-side distal surface portion 62 is the arc-shaped jaw-side curved surface having the constant curvature R2 when viewed from one of the open/close directions of the jaw 32. In the jaw-side inclined plane 67, the acute angles (β1 and β2) between the tangential lines (U1 and U2) of the jaw-side inclined plane 67 and the longitudinal axis C increase as it goes from the first perpendicular direction toward the second perpendicular direction when viewed from one of the open/close directions of the jaw 32. Such a configuration of the jaw-side inclined plane 67 allows a greater range in which the jaw 32 can be in surface contact with the living tissue S with a suitable magnitude (about 30 to 80°) of angle θ2 between the jaw 32 and the living tissue S. Therefore, bipolar treatments can be performed at various positions of the living tissue S by making one hole H in the body wall D.

In the bipolar treatment device 1, curvature R2 of the jaw-side inclined plane 67 is substantially the same as curvature R1 of the inclined plane 53 of the probe 3 when viewed from one of the open/close directions of the jaw 32. That is, the jaw-side inclined plane 67 is formed into a shape corresponding to the inclined plane 53 of the probe 3. It is thus possible to easily bring the probe 3 into surface contact with the living tissue S with a suitable magnitude of angle θ1 between the probe 3 and the living tissue S, and to also easily bring the jaw 32 into surface contact with the living tissue S with a suitable magnitude of angle θ2 between the jaw 32 and the living tissue S simultaneously. Accordingly, operability at the time of the bipolar treatment can be improved.

In the probe 3 of the bipolar treatment device 1, the suction path 26 is formed to extend to the distal surface portion 25 along the longitudinal axis C. The opening direction at the distal end of the suction path 26 is parallel to the longitudinal axis C. In the ultrasonic suction device (1) generally used by the operator, the opening direction at the distal end of the suction path (26) is parallel to the longitudinal axis C, as in the probe 3 according to the present embodiment. Thus, the operator can efficiently perform the ultrasonic suction treatment.

The probe 3 can only be manufactured by perforation and milling, and bending is not needed to manufacture the probe 3. As there are no adverse effects of an internal stress resulting from bending, the probe 3 can be easily manufactured with low costs and with stable quality.

In the probe 3 of the bipolar treatment device 1, the suction path 26 extends to the distal surface portion 25, and the opening direction at the distal end of the suction path 26 is parallel to the longitudinal axis C. Thus, the liquid supplied from the liquid supply path 38 is not easily suctioned into the suction path 26. Therefore, a liquid such as a physiological saline solution can be stably supplied in the ultrasonic suction treatment.

In the bipolar treatment device 1 having such a configuration, the opening at the distal end of the suction path 26 is formed so that it goes toward the distal direction side as it goes from the first perpendicular direction toward the second perpendicular direction. Thus, even if suction from the opening of the suction path 26 is performed at the same time when the living tissue is resected by cavitation, the living tissue or the like that is not shattered by the cavitation does not easily adhere to the opening. As the suction path 26 is not curved, the living tissue or the like is not easily retained in the suction path 26. Therefore, the suction can be stably performed in the ultrasonic suction.

In the bipolar treatment device 1, the inclined plane 53 of the distal surface portion 25 is an arc-shaped curved surface having the constant curvature R1 when viewed from one of the open/close directions of the jaw 32. In the inclined plane 53, the acute angles (α1 to α3) between the tangential lines (T1 to T3) of the inclined plane 53 and the longitudinal axis C increase as it goes from the first perpendicular direction toward the second perpendicular direction when viewed from one of the open/close directions of the jaw 32. In the distal surface portion 25, cavitation is more efficiently caused by ultrasonic vibrations in parts where the acute angles (α1 to α3) between the tangential lines (T1 to T3) of the distal surface portion 25 (inclined plane 53) and the longitudinal axis C are greater when viewed from one of the open/close directions of the jaw 32. In the probe 3, the second end position X2 of the inclined plane 53 is located to the second perpendicular direction side of the second root position Y2 of the second protrusion 52. Thus, in the part of the inclined plane 53 on the second perpendicular direction side, the acute angles (α1 to α3) between the tangential lines (T1 to T3) of the inclined plane 53 and the longitudinal axis C are greater when viewed from one of the open/close directions of the jaw 32. As a result, in the part of the inclined plane 53 on the second perpendicular direction side, cavitation is more efficiently caused by ultrasonic vibrations. Therefore, the living tissue can be efficiently and safely resected in the ultrasonic suction.

Modifications of First Embodiment

Although the first end position X1 of the inclined plane 53 corresponds to the end of the outer peripheral distal end P1 of the outer peripheral portion 21 on the first perpendicular direction side according to the first embodiment, the present invention is not limited thereto. For example, as a first modification, the distal surface portion 25 may include a perpendicular plane 79 which is provided to the first perpendicular direction side of the inclined plane 53, and which is perpendicular to the longitudinal axis C, as shown in FIG. 21. In this modification, the first end position X1 of the inclined plane 53 is located to the first perpendicular direction side of the first root position Y1 of the first protrusion 51. The second end position X2 of the inclined plane 53 is located to the second perpendicular direction side of the suction path 26. Such a configuration allows the surface area of the inclined plane 53 to be increased without the increase of the probe 3 in size and weight even when the suction path 26 is provided inside.

That is, according to the first modification, the probe 3 has only to include the first protrusion 51 which protrudes the outer peripheral distal end P1 of the outer peripheral portion 21 toward the first perpendicular direction, which is perpendicular to the longitudinal axis C and perpendicular to the open/close direction of the jaw 32. The first end position X1 of the inclined plane 53 has only to be located to the first perpendicular direction side of the first root position Y1 of the first protrusion 51.

Figure 22:
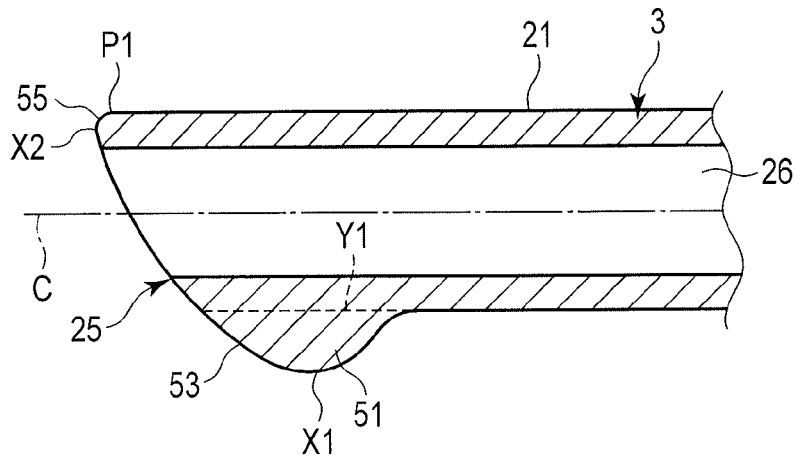
FIG. 22 is a schematic sectional view showing the configuration of a distal portion of a probe according a second modification of the first embodiment.

Although the second protrusion 52 is provided according to the first embodiment, the present invention is not limited thereto. For example, as a second modification, the probe 3 may include no second protrusion 52, as shown in FIG. 22. Again in this modification, the first end position X1 of the inclined plane 53 is located to the first perpendicular direction side of the first root position Y1 of the first protrusion 51. The second end position X2 of the inclined plane 53 is located to the second perpendicular direction side of the suction path 26.

That is, according to the second modification, the probe 3 has only to include the first protrusion 51 which protrudes the outer peripheral distal end P1 of the outer peripheral portion 21 toward the first perpendicular direction, which is perpendicular to the longitudinal axis C and perpendicular to the open/close direction of the jaw 32. The second end position X2 of the inclined plane 53 has only to be located to the second perpendicular direction side of the suction path 26.

Figure 23:
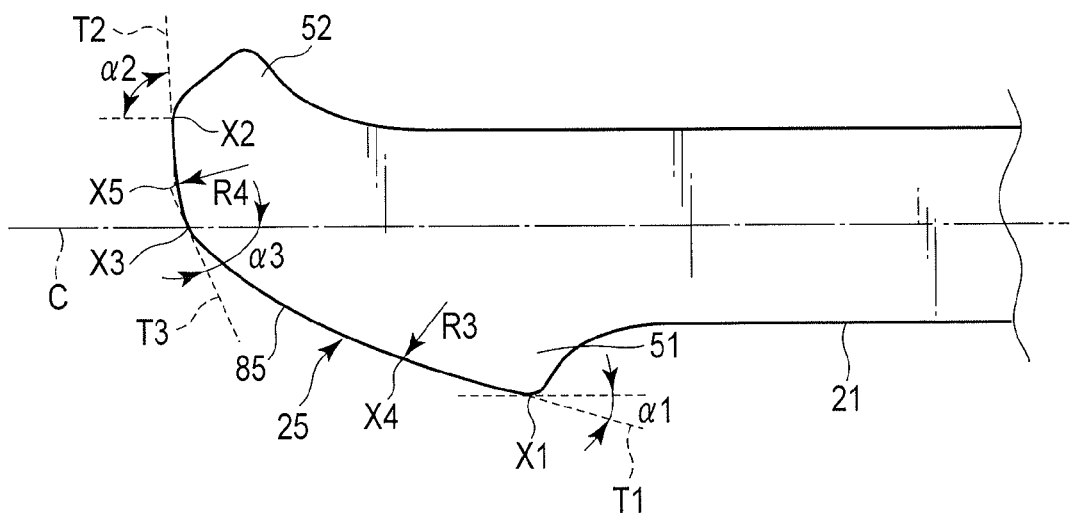
FIG. 23 is a schematic diagram showing a distal portion of a probe according to a third modification of the first embodiment when viewed from one of open/close directions of the jaw.

Although the inclined plane 53 of the distal surface portion 25 is a curved surface having the constant curvature R1 when viewed from one of the open/close directions of the jaw 32 according to the first embodiment, the present invention is not limited thereto. For example, as a third modification, the distal surface portion 25 may include an inclined plane 85 which varies in curvature by the position when viewed from one of the open/close directions of the jaw 32, as shown in FIG. 23. The curvature is R3 at a position X4 of the inclined plane 85, and the curvature is R4 at a position X5 located to the first perpendicular direction side of the position X4. However, in the inclined plane 85, the acute angles ($\alpha 1$ to $\alpha 3$) between the tangential lines (T1 to T3) of the inclined plane 85 and the longitudinal axis C increase as it goes from the first perpendicular direction toward the second perpendicular direction when viewed from one of the open/close directions of the jaw 32, as in the inclined plane 53 according to the first embodiment. This allows a greater range in which the probe 3 can be in surface contact with the living tissue S with a suitable magnitude (about 30 to 80°) of angle $\theta 1$ between the probe 3 and the living tissue S, as in the first embodiment. Therefore, bipolar treatments can be performed at various positions of the living tissue S by making one hole H in the body wall D.

That is, according to the third modification, the inclined plane (53, 85) has only to be a curved surface in which the acute angles ($\alpha 1$ to $\alpha 3$) between the tangential lines (T1 to T3) of the inclined plane 53 and the longitudinal axis C increase as it goes from the first perpendicular direction toward the second perpendicular direction when viewed from one of the open/close directions of the jaw 32.

According to the first embodiment, the inclined plane 53 of the distal surface portion 25 is an arc-shaped curved surface having the constant curvature R1 when viewed from one of the open/close directions of the jaw 32. In the inclined plane 53, the acute angles ($\alpha 1$ to $\alpha 3$) between the tangential lines (T1 to T3) of the inclined plane 53 and the longitudinal axis C increase as it goes from the first perpendicular direction toward the second perpendicular direction when viewed from one of the open/close directions of the jaw 32. However, as a fourth modification, the distal surface portion 25 may include, instead of the inclined plane 53, an inclined plane 81 in a planar form, as shown in FIG. 24A. As the inclined plane 53, in the inclined plane 81, it goes toward the distal direction side as it goes from the first perpendicular direction toward the second perpendicular direction. The first end position X1 of the inclined plane 81 is located to the first perpendicular direction side of the first root position Y1 of the first protrusion 51. The second end position X2 of the inclined plane 81 is located to the second perpendicular direction side of the suction path 26.

FIG. 24B is a diagram showing the contact between the probe 3 and the living tissue S at various positions of the living tissue S when a bipolar treatment is performed while the jaw 32 is open with respect to the probe 3 according to this modification. As shown in FIG. 24B, when a bipolar treatment is performed, the hole H is made in the body wall D, and the probe 3 is inserted into a body cavity from the hole H. In this modification, the inclined plane 81 of the distal surface portion 25 is a plane. Therefore, as compared with the probe 3 including the inclined plane 53 according to the first embodiment, the probe 3 can be in surface contact with the living tissue S in a smaller range with a suitable magnitude (about 30 to 80°) of angle $\theta 1$ between the probe 3 and the living tissue S. For example, when the probe 3 according to the first embodiment is used, the probe 3 can be in surface contact with the living tissue S with a suitable magnitude of angle $\theta 1$ between the probe 3 and the living tissue S at all positions Q1 to Q3 of the living tissue S (see FIG. 16). In contrast, when the probe 3 according to this modification is used, the probe 3 can only be in surface contact with the living tissue S with a suitable magnitude of angle $\theta 1$ between the probe 3 and the living tissue S at position Q2 of the living tissue S (see FIG. 24B). That is, at positions Q1 and Q3 of the living tissue S, the probe 3 cannot be in surface contact with the living tissue S with a suitable magnitude of angle $\theta 1$ between the probe 3 and the living tissue S.

As described above, in this modification, when one hole H is made in the body wall D, the probe 3 can be in surface contact with the living tissue S in a smaller range with a suitable magnitude (about 30 to 80°) of angle $\theta 1$ between the probe 3 and the living tissue S than in the first embodiment. However, when a bipolar treatment is only performed in a particular part (for example, position Q2) of the living tissue S, a bipolar treatment can be efficiently performed by using the jaw 32 opened with respect to the probe 3 and the probe 3 as electrodes even if the probe 3 according to this modification is used. Therefore, the living tissue S is efficiently coagulated in the particular part (for example, position Q2) of the living tissue S.

That is, according to the fourth modification, in the inclined plane (53, 81) of the distal surface portion 25, it has only to go toward the distal direction side as it goes from the first perpendicular direction toward the second perpendicular direction. The first end position X1 of the inclined plane (53, 81) has only to be located to the first perpendicular direction side of the first root position Y1 of the first protrusion 51. The second end position X2 of the inclined plane (53, 81) has only to be located to the second perpendicular direction side of the suction path 26.

The bipolar treatment device 1 may also be used as an ultrasonic coagulation-and-cutting device which is configured to coagulate and cut living tissue such as a blood vessel held between the probe 3 and the jaw 32. In this case, frictional heat is generated between the probe 3 and the living tissue S by the ultrasonic vibrations of the probe 3 while the tissue is held between the probe 3 and the jaw 32. The living tissue is cut by the generated frictional heat. The living tissue is also reformed by the passage of a high-frequency current through the living tissue between the jaw 32 and the distal portion of the probe 3. As a result, the living tissue is coagulated.

Second Embodiment

Now, a second embodiment of the present invention is described with reference to FIG. 25. In the second embodiment, the configuration according to the first embodiment is modified as described below. The same parts as those according to the first embodiment are provided with the same reference marks and are not described.

FIG. 25 is a diagram showing a distal portion of a probe 3 according to the present embodiment. As shown in FIG. 25, a distal surface portion 25 of the probe 3 includes an inclined plane 53, as in the first embodiment. The inclined plane 53 is an arc-shaped curved surface having a constant curvature R1 when viewed from one of the open/close directions of a jaw 32. In the inclined plane 53, acute angles ($\alpha1$ to $\alpha3$) between tangential lines (T1 to T3) of the inclined plane 53 and a longitudinal axis C increase as it goes from a first perpendicular direction to a second perpendicular direction when viewed from one of the open/close directions of the jaw 32. A first end position X1 of the inclined plane 53 corresponds to the end of an outer peripheral distal end P1 of an outer peripheral portion 21 on the first perpendicular direction side. A second end position X2 of the inclined plane 53 corresponds to the end of the outer peripheral distal end P1 of the outer peripheral portion 21 on the second perpendicular direction side. In the present embodiment, the distal surface portion 25 includes no curved surface 55.

Accordingly, the bipolar treatment device 1 having the configuration described above provides the following advantageous effects in addition to the advantageous effects similar to those according to the first embodiment. That is, in the probe 3 of the bipolar treatment device 1 according to the present embodiment, the second end position X2 of the inclined plane 53 corresponds to the end of the outer peripheral distal end P1 of the outer peripheral portion 21 on the second perpendicular direction side. Thus, the surface area of the inclined plane 53 can be greater. Consequently, the probe 3 can be more easily brought into surface contact with living tissue S with a suitable magnitude of an angle $\theta1$ between the probe 3 and the living tissue S.

In the probe 3, the second end position X2 of the inclined plane 53 corresponds to the end of the outer peripheral distal end P1 of the outer peripheral portion 21 on the second perpendicular direction side. Thus, in a part of the inclined plane 53 on the second perpendicular direction side, the acute angles ($\alpha1$ to $\alpha3$) between the tangential lines (T1 to T3) of the inclined plane 53 and the longitudinal axis C are greater when viewed from one of the open/close directions of the jaw 32. Therefore, cavitation is more efficiently caused by ultrasonic vibrations in the part of the inclined plane 53 on the second perpendicular direction side. Consequently, the living tissue can be more efficiently and safely resected in the ultrasonic suction.

Third Embodiment

Now, a third embodiment of the present invention is described with reference to FIG. 26. In the third embodiment, the configuration according to the first embodiment is modified as described below. The same parts as those according to the first embodiment are provided with the same reference marks and are not described.

FIG. 26 is a diagram showing the configuration of a distal portion of a probe 3 according to the present embodiment. As shown in FIG. 26, a distal surface portion 25 of the probe 3 includes an inclined plane 53, as in the first embodiment. The inclined plane 53 is an arc-shaped curved surface having a constant curvature R1 when viewed from one of the open/close directions of a jaw 32. In the inclined plane 53, acute angles ($\alpha1$ to $\alpha3$) between tangential lines (T1 to T3) of the inclined plane 53 and a longitudinal axis C increase as it goes from a first perpendicular direction to a second perpendicular direction when viewed from one of the open/close directions of the jaw 32. A first end position X1 of the inclined plane 53 corresponds to an end of an outer peripheral distal end P1 of an outer peripheral portion 21 on the first perpendicular direction side. A second end position X2 of the inclined plane 53 is located to the second perpendicular direction side of a second root position Y2 of a second protrusion 52.

The distal surface portion 25 includes a perpendicular plane 82 which extends from the second end position X2 of the inclined plane 53 toward the second perpendicular direction, and which is perpendicular to the longitudinal axis C. The perpendicular plane 82 extends from the second end position X2 to an end of the outer peripheral distal end P1 of the outer peripheral portion 21 on the second perpendicular direction side. In the present embodiment, the distal surface portion 25 includes no curved surface 55.

In the distal surface portion 25, cavitation is more efficiently caused by ultrasonic vibrations in a surface perpendicular to the longitudinal axis C than in a surface inclined with respect to the longitudinal axis C. In the distal surface portion 25 according to the present embodiment, the perpendicular plane 82 is provided, so that cavitation is more efficiently caused by ultrasonic vibrations. Consequently, the living tissue can be more efficiently and safely resected in the ultrasonic suction.

Accordingly, the bipolar treatment device 1 having the configuration described above provides the following advantageous effects in addition to the advantageous effects similar to those according to the first embodiment. That is, in the probe 3 of the bipolar treatment device 1 according to the present embodiment, the distal surface portion 25 includes the perpendicular plane 82 perpendicular to the longitudinal axis C. In the distal surface portion 25, cavitation is more efficiently caused by ultrasonic vibrations in the surface perpendicular to the longitudinal axis C than in the surface inclined with respect to the longitudinal axis C.

Therefore, by providing the perpendicular plane 82, cavitation is more efficiently caused by ultrasonic vibrations in the distal surface portion 25. Consequently, the living tissue can be more efficiently and safely resected in the ultrasonic suction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment device comprising:
    a probe having a proximal end and a distal end and extending along a straight longitudinal axis,
    the probe including:
        a distal outer surface configured to form the distal end of the probe and an inclined plane provided on the distal outer surface of the probe such that the inclined plane is inclined relative to the straight longitudinal axis and includes a distal most section;
        a suction path extending inside the probe along the straight longitudinal axis, consisting of a single suction path opening disposed on the inclined plane proximal to the distal most section; and
        a first protrusion disposed on the probe and configured to protrude from a first root position on the inclined plane toward a first direction perpendicular to the straight longitudinal axis;
    a jaw configured to open along an opening direction and close along a closing direction relative to the distal end of the probe, the opening direction and the closing direction traversing the straight longitudinal axis such that the opening direction is opposite to the closing direction, and
    the jaw being configured to open and close to grasp a grasping target between the jaw and the distal end of the probe and configured to treat the grasping target, such that the grasping target contacts both the distal portion of the probe and the jaw during treatment,
    wherein:
        the first direction traverses the straight longitudinal axis and is perpendicular to the opening direction and the closing direction of the jaw,
        the first protrusion is configured to form a part of the distal outer surface of the probe, and
        the first root position is positioned to a first-perpendicular-direction-side with regard to the single suction path opening; and
        a first-perpendicular-direction-side-end of the inclined plane being disposed on the first-perpendicular-direction-side with regard to the first root position,
        a second-perpendicular-direction-side-end of the inclined plane being disposed on a second-perpendicular-direction-side with regard to the single suction path opening so that the distal outer surface is asymmetrical about a referential plane that passes through the straight longitudinal axis and that is perpendicular to the first direction and a second direction perpendicular to the straight longitudinal axis, the second direction being opposite to the first direction, and
        the second-perpendicular-direction-side-end of the inclined plane being located on a distal side with regard to the first-perpendicular-direction-side-end of the inclined plane, the inclined plane extending toward the distal side from the first-perpendicular-direction-side-end to the second-perpendicular-direction-side-end, and the inclined plane extending toward the distal side from the single suction path opening to the second-perpendicular-direction-side.

2. The energy treatment device according to claim 1, wherein
    the probe is configured to transmit at least one of an ultrasonic vibration and a high-frequency current.

3. The energy treatment device according to claim 1, further comprising
    a second protrusion disposed on the probe and configured to protrude from a second root position on the inclined plane toward the second direction,
    the second protrusion being configured to form a part of the distal outer surface of the probe opposite to the first protrusion,
    the second root position being positioned to the second perpendicular direction side with regard to the single suction path opening, and
    the second-perpendicular-direction-side end of the inclined plane being disposed on the second perpendicular direction side with regard to the second root position.

* * * * *

UNITED STATES PATENT AND TRADEMARK OFFICE
CERTIFICATE OF CORRECTION

| | |
|---|---|
| PATENT NO. | : 9,474,568 B2 |
| APPLICATION NO. | : 13/630952 |
| DATED | : October 25, 2016 |
| INVENTOR(S) | : Tsunetaka Akagane |

It is certified that error appears in the above-identified patent and that said Letters Patent is hereby corrected as shown below:

On the Title Page

Item (54) and in the Specification, Column 1, Line 1, change --ENERGY BIPOLAR TREATMENT DEVICE-- to --ENERGY TREATMENT DEVICE--

Signed and Sealed this
Third Day of January, 2017

Michelle K. Lee
*Director of the United States Patent and Trademark Office*